(12) United States Patent
Dowling et al.

(10) Patent No.: US 7,897,031 B2
(45) Date of Patent: Mar. 1, 2011

(54) CONTROL APPARATUS, SYSTEM, AND METHOD FOR REDUCTION AND/OR PREVENTION OF SPACE WEATHER INDUCED CORROSION

(75) Inventors: David B. Dowling, Coconut Grove, FL (US); Farshad Khorrami, Brooklyn, NY (US); Joseph G. Michels, New York, NY (US); Mikhail Panasyuk, Moscow (RU)

(73) Assignee: Applied Semiconductor International Ltd., Neuenhof (CH)

( * ) Notice: Subject to any disclaimer, the term of this patent is extended or adjusted under 35 U.S.C. 154(b) by 32 days.

(21) Appl. No.: 12/273,167

(22) Filed: Nov. 18, 2008

(65) Prior Publication Data

US 2010/0025261 A1 Feb. 4, 2010

Related U.S. Application Data

(63) Continuation of application No. 11/908,914, filed as application No. PCT/US2006/009705 on Mar. 17, 2006, now abandoned.

(60) Provisional application No. 60/662,354, filed on Mar. 17, 2005.

(51) Int. Cl.
*C23F 13/04* (2006.01)
*C23F 13/22* (2006.01)

(52) U.S. Cl. .................. 205/725; 205/724; 205/730; 205/731; 205/734; 205/735; 205/736; 205/740; 204/196.02; 204/196.04; 204/196.06; 204/196.07; 204/196.11; 204/196.12; 204/196.16; 204/196.26; 204/196.37

(58) Field of Classification Search ........... 204/196.02, 204/196.04, 196.06, 196.07, 196.11, 196.12, 204/196.16, 196.26, 196.37; 205/724, 725, 205/730, 731, 734, 735, 736, 740
See application file for complete search history.

(56) References Cited

U.S. PATENT DOCUMENTS

| 6,325,915 B1 | 12/2001 | Dowling et al. |
| 6,402,933 B1 | 6/2002 | Dowling |
| 6,551,491 B2 | 4/2003 | Dowling et al. |
| 6,562,201 B2 | 5/2003 | Dowling |
| 6,811,681 B2 * | 11/2004 | Dowling et al. ............ 205/725 |
| 6,890,420 B2 | 5/2005 | Dowling |
| 7,029,569 B2 | 4/2006 | Dowling et al. |
| 7,318,889 B2 | 1/2008 | Dowling |
| 2007/0023295 A1 | 2/2007 | Dowling |

OTHER PUBLICATIONS

U.S. Appl. No. 12/206,210, filed Sep. 8, 2008, Bocarsly, et al.

(Continued)

*Primary Examiner*—Bruce F Bell
(74) *Attorney, Agent, or Firm*—Oblon, Spivak, McClelland, Maier & Neustadt, L.L.P.

(57) ABSTRACT

An apparatus, system, method and computer program product directed to controlling corrosion, particularly space weather induced corrosion, of a conductive structure in contact with a corrosive environment and coated with a semiconductive coating, where the corrosion is controlled by a controllable filter and a corresponding electronic control unit configured to process and adjust the controllable filter in response to at least one measured parameter associated with space weather effects on the conductive structure.

50 Claims, 16 Drawing Sheets

OTHER PUBLICATIONS

U.S. Appl. No. 11/908,914, filed Sep. 17, 2007, Dowling, et al.
U.S. Appl. No. 10/401,149, filed Mar. 28, 2003, Dowling, et al.
U.S. Appl. No. 10/271,734, filed Oct. 17, 2002, Dowling.

Antti Pulkkinen, et al. "Modelling of space weather effects on pipelines", Journal of Applied Geophysics, vol. 48, XP-002541922, 2001, pp. 233-256.

* cited by examiner ized to prevent the flow of corrosion current or electrons between the naturally occurring anodes and cathodes or within galvanic couples. Each of these processes provided limited success. Coatings by far represent the most wide-spread method of general corrosion prevention (see Leon et al U.S. Pat. No. 3,562,124 and Hayashi et al U.S. Pat. No. 4,219,358). Cathodic protection, however, has been used to protect hundreds of thousands of miles of pipe and acres of steel surfaces subject to buried or immersion conditions.

CONTROL APPARATUS, SYSTEM, AND METHOD FOR REDUCTION AND/OR PREVENTION OF SPACE WEATHER INDUCED CORROSION

CROSS REFERENCE TO RELATED PATENT DOCUMENT

This application is related to U.S. Pat. Nos. 6,325,915, 6,402,933, 6,551,491, 6,562,201, 6,811,681 and copending U.S. application Ser. No. 10/978,352, filed on Nov. 2, 2004, the entire contents of each being incorporated herein by reference.

BACKGROUND OF THE INVENTION

1. Field of the Invention

The present invention relates to a control apparatus, system, and method for controlling a semiconductor-based corrosion prevention system for preventing corrosion induced by space weather effects and corresponding changes in geopotentials.

2. Discussion of the Background Art

The annual cost of metallic corrosion in the United States economy is approximately $300 billion, according to a report released by Battelle and the Specialty Steel Industry of North America entitled "Economic Effects of Metallic Corrosion in the United States," dated 1995, the entire contents of which is hereby incorporated by reference. The report estimates that about one-third of the cost of corrosion ($100 billion) is avoidable and could be saved by broader application of corrosion-resistant materials and application of best anti-corrosive practice from design through maintenance. The estimates result from a partial update by Battelle scientists of the findings of a study conducted by Battelle and the National Institute of Standards and Technology titled "Economic Effects of Metallic Corrosion in the United States," the entire contents of which are hereby incorporated by reference. The original work in 1978 included an estimate that, in 1975, metallic corrosion cost the U.S. $82 billion (4.9 percent of the Gross National Product), and approximately $33 billion was avoidable because best practices were not used at the time.

A variety of methods for controlling corrosion have evolved over the past several centuries, with particular emphasis on methods to extend the life of metallic structures in corrosive environments. These methods typically include protective coatings, which are used principally to upgrade the corrosion resistance of ferrous metals, such as steel, and some nonferrous metals, such as aluminum, and to avoid the necessity for using more costly alloys. Thus, they both improve performance and reduce costs. However, such protective coatings typically have several pitfalls, including poor applicability and limited lifetimes.

Protective coatings fall into three main categories. The largest of these categories is the topical coating such as a paint that acts as a physical barrier against the environment. The second category consists of sacrificial coatings, such as zinc or cadmium that are designed to act as a sacrificial anode, preferentially corroding in order to save the base metal from attack. The third category consists of cathodic protection systems.

Cathodic protection and coatings are both engineering disciplines with a primary purpose of mitigating and preventing corrosion. Each process is different: cathodic protection prevents corrosion by introducing an electrical potential from external sources to counteract the normal electrical chemical corrosion reactions whereas coatings form a barrier to prevent Cathodic protection is used to reduce the corrosion of the metal surface by providing it with enough cathodic current to make its anodic dissolution rate become negligible (for examples, see Pryor U.S. Pat. No. 3,574,801; Wasson U.S. Pat. No. 3,864,234; Maes U.S. Pat. No. 4,381,981; Wilson et al U.S. Pat. No. 4,836,768; Webster U.S. Pat. No. 4,863,578; and Stewart et al U.S. Pat. No. 4,957,612). Cathodic protection operates by extinguishing the potential difference between the local anodic and cathodic surfaces through the application of sufficient current to polarize the cathodes to the potential of the anodes. In other words, the effect of applying cathodic currents is to reduce the area that continues to act as an anode, rather than reduce the rate or corrosion of such remaining anodes. Complete protection is achieved when all of the discrete anodes have been extinguished. From an electrochemical standpoint, this indicates that sufficient electrons have been supplied to the metal to be protected, so that any tendency for the metal to ionize or go into solution has been neutralized.

Recent work in the study of corrosion has found that electrochemical corrosion processes appear to be associated with random fluctuations in the electrical properties of electrochemical systems, such as cell current and electrode potential. These random fluctuations are known in the art as "noise." About 20 years ago, scientists found that all conductive materials begin corroding as soon as they are produced due to electrochemical activity caused by impurities in the material. It was later found that this activity could be monitored using electronic instruments detecting the current generated, now commonly referred to as "corrosion noise." Essentially, the greater the magnitude of this current, the "noisier" the material and the faster the rate of corrosion. For example, steel is "noisier" than bronze and corrodes at a faster rate. Researchers have begun to apply noise analysis techniques to study the processes of corrosion in electrochemical systems.

Further, researchers have more recently been studying the effects of geomagnetically induced currents (GIC) and the interaction between the solar wind and Earth's magnetic field on ground based structures, particularly conducting structures of significant size and/or length, such as pipelines or transmission lines and towers. This interaction between the solar wind and the Earth's magnetic field produces time varying currents in the ionosphere and magnetosphere, resulting in variations of the geomagnetic field at the surface of the earth and inducing an electric field which drives currents in such large structures, particularly in structures such as oil and gas pipelines. Solar events also have the effect of changing the local geopotential, in effect changing the electrical characteristics of "ground." These GIC's interfere with cathodic protection schemes and electrical surveys of pipelines, and independently, have been proposed as contributors to pipeline corrosion (Pulkkinen et al, *J. Appl. Geophys.*, 48, 233-256 (2001)). Time-variable conditions in the space environment affecting space-borne and ground-based technological systems are collectively known as "space weather", a topic that has been the focus of much study in recent years (see, for example, Plunkett et al, *IEEE Transactions on Plasma Sci-* ence 28(6), 1807-17) and references therein, Pulkkinen et al, supra; Pulkkinen et al, *J. Appl. Geophys.*, 48, 219-231 (2001); Pirjola et al, *Adv. Space Res.*, 26(1), 5-14 (2000); Boteler, *Adv. Space Res.*, 26(1), 15-20 (2000); and Tkachenko, *Protection of Metals*, 36(2), 196-198 (2000) translated from *Zashchita Metallov*, 36(2), 222-224 (2000); the contents of each of these references are hereby incorporated by reference). These studies have focused on observing, recording and modeling the effects of such space weather on the Earth's magnetic and electric fields, as well as man-made structures such as pipeline systems and the resulting corrosion that may be induced by such space weather effects. However, while the effects of space weather in accelerating corrosion are well documented, there has been no viable suggestion on how to prevent the acceleration of corrosion caused by such space weather effects.

Pipelines are, typically, long electrical conductors buried anywhere from a few feet to a few tenths of a foot below ground. They can run thousands of miles crossing soils of varying resistivities. Any variation in the magnetic field around the pipeline can induce significant current on the pipeline. One such source that causes variations in the magnetic field that surrounds the pipeline is "magnetic storm" activity, such as the above described space weather effects. This is different from the earth's own magnetic field in that it is "external" in nature. This induced current, also known as "Telluric Currents" in the pipeline industry, can cause significant swings in Pipe-to-soil Potentials (PSP). This variation in PSP is documented in the pipeline industry and could be as high as 1000 mV. There are several concerns with regard to the swings in the PSP arising from telluric currents:

a. PSP swings more positive than −850 mV ($CuCuSO_4$) may result in corrosion.
b. PSP swings more negative than −1200 mV ($CuCuSO_4$) result in hydrogen generation at the metal coating interface that can lead to coating disbandment.
c. Interference with PSP surveys.
d. Possible damage to electronic equipment connected to the pipeline.

Though the concept of telluric currents is simple, the pipeline system's response to the magnetic storm is rather complicated. This is due to the fact that the whole pipeline system is complex in nature. It typically consists of a) gathering systems from the oil and gas fields; b) transmission systems between cities, typically two parallel pipelines that travel long distances; c) variation in the soil resistivity along the pipe route d) a distribution network within a city or populated area; e) presence of bends and insulating flanges; f) presence of coatings; and other details.

Pipeline operators have long used coatings as a way to reduce the overall corrosion. However, coatings alone have no effect on reducing the telluric currents, and may, in fact, magnify the damage.

Pipeline operators have generally believed that although telluric currents may be intense for a short period of time, they seldom result in as significant a corrosion as uncontrolled manmade stray currents. However, recent data have shown that variation in PSP due to telluric currents may be such that it can result in significant corrosion and metal loss that could be an order of magnitude higher (Osella, 1999) than the corrosion rate during the quiet period. Thus, telluric effects may not be easily counteracted with the typical cathodic protection system.

Pipeline operators deal with this phenomenon by allowing the telluric current to flow along the pipeline and drain through the ground connections placed at strategic locations along the pipeline. This requires that they bond across the insulating joints of the pipeline. Insulating joints are placed along the pipelines to reduce the probability of stray current pick up by reducing the length of continuous section of the pipelines (i.e. metallic path). The effectiveness of grounding the pipeline to harmlessly discharge the telluric currents is disputed by researchers due to the fact that this can actually increase the effects of stray current pick up. Pipeline operators are thus faced with two unsatisfactory options: bond across the insulating joints and ground the pipeline or keep the pipe segmented with each section separated by insulated joints. The former scheme has the effect of turning the entire pipeline into a giant collector for stray currents induced by space weather; the latter leaves the pipeline vulnerable to telluric currents. Neither option obviates space weather induced corrosion.

Riffe, U.S. Pat. No. 5,352,342 and Riffe, U.S. Pat. No. 5,009,757, the contents of each of which being incorporated herein by reference, disclose a zinc/zinc oxide based silicate coating that is used in combination with electronics in a corrosion prevention system. The zinc/zinc oxide particles in the coating are disclosed as having semiconductor properties, primarily a p-n junction at the Zn—ZnO phase boundary. When reverse biased, this p-n junction is described as behaving as a diode and inhibiting electron transfer across the boundary. This restriction limits electron transfer from sites of Zn oxidation to the sites of oxygen reduction on the ZnO surface. Effectively, there is increased resistance between the anode and cathode of local corrosion cells and corrosion is reduced.

On average, the Zn—ZnO based junction will be reversely biased due to the potentials associated with the oxidation of Zn at the Zn surface and the reduction of $O_2$ at the ZnO surface. However, significant stochastic voltage fluctuations occur. These voltage fluctuations cause the junction to episodically become forward biased. When forward biased, electron transfer across the junction increases and there is an acceleration or "burst" of the oxidation of Zn and reduction of $O_2$. Effectively, there is a short circuit between the anode and cathode of local corrosion cells and corrosion is enhanced.

The Riffe patents disclose attachment of a fixed value capacitor in the electrochemical circuit of the corrosion prevention system. However, as recognized by the present inventors, there is no recognition of the desirability of controlling the level of capacitance nor any method suggested for determining how to dynamically change the value of capacitance needed to effectively prevent corrosion in any given structure or an optimal way to determine the value of the capacitance needed, particularly in the event of a space weather disturbance.

One drawback to previous corrosion preventive methods, such as that of Riffe disclosed above, is the relative inflexibility of color selection available for the silicate based coatings disclosed therein, with the only color readily available being gray. While this is acceptable in most marine and structural uses, there is a need for corrosion preventive coatings that are non-sacrificial and which can be provided in a range of colors for use as paint substitutes, particularly in the automotive and transportation industries. These and other drawbacks are largely overcome with the semiconductor coatings and related systems of Dowling's U.S. Pat. Nos. 6,325,915, 6,402,933, 6,551,491 and U.S. Pat. No. 6,562,201, the entire contents of each hereby incorporated by reference. The semiconductive coating and system of the Dowling patents and application can be used with a variety of conductive substrates to provide an array of interesting properties. With the semiconductor always being a material less noble than the substrate on which it is applied, the coating stabilizes the potential of the protected material. The electrons produced by the electrochemical activity are transferred from the protected substrate to the semiconductor of the coating or, simply, the corrosion noise is transferred from the protected material to the coating.

FIG. 1 is a representation of electrochemical noise present in untreated metal 101 the randomly fluctuating voltage is measured and displayed as waveform 102 (shown as a sawtooth waveform, but an actual waveform would have broader band components and would be stochastic in nature).

FIG. 2 shows the effect of applying a semiconductive protective coating on a metal surface so as to prevent corrosion and fouling where the coating 210 comprises a material less noble than the metal 201 it is protecting. Because the coating 210 is less noble than the metal 201, it subsumes the electrochemical noise 211 that would be present in the metal but for the coating this result is displayed 202 as a flat waveform in the metal. Individual semiconductor particles within the coating 250 are responsible for the anti-corrosion properties of the coating.

FIG. 3 is a representation of a layered semiconductor/metal composition. When doped with zinc, the anti-corrosion capabilities of the semiconductor material for steel (ferrous alloys) results from the establishment of a potential due to Zn oxidation and oxygen reduction, referred to as "corrosion potential." In this respect, the system acts as a conventional sacrificial anodic material with iron oxidation suppressed at the potential established by the Zn oxidation. However, Zn oxidation in a semiconductor is significantly reduced or passivated, with a reduction of the corrosion potential, resulting in the extreme long life of the coating. The passivation is a result of a combination of the varistor-like behavior of the Zn/ZnO boundary and an associated filter's ability to maintain a potential difference across the boundary, such that the boundary has a high electrical resistance. A semiconductor particle 250 is comprised of two regions: a P-type region 320 and an N-type region 310 with a junction 330 that behaves as a varistor with electron flow 302 between the two regions. When using zinc, the zinc particles are covered by a zinc oxide layer with the various oxide coated particles surrounded by a conductive binder. The boundary of the P and N semiconductors in the semiconductive coating acts as a varistor (back to back diodes) that controls the flow of electrons between them. Proper application of a current to the semiconductive coating, connected to the protected substrate, stabilizes the potential at this boundary. This slows the rate of electron transfer from the P to the N semiconductor, reducing its rate of corrosion by a factor of $10^3$, yielding an extension in the life of the semiconductive coating that can exceed the design life of the treated object.

Varistors (variable resistors) have highly non-linear electrical characteristics and are functionally equivalent to back-to-back diodes. In a voltage limited region, the "switch region," they pass only a leakage current. When the voltage magnitude exceeds the switch voltage, for instance during a transient, the varistor becomes highly conducting. Varistors are commonly based on ZnO. FIG. 4 is a graph representing the current voltage relationship for varistor, within which an axis representing voltage 1101, an axis representing current 1102, and a curve representing current 1103 over a range of biasing voltage are displayed. The range between $-V_b$ 1110 and $V_b$ 1107 represents the voltage region 1104 in which the varistor behaves as a switch. The point along the curve labeled $I_L$ 1105 is the point along the curve that corresponds to leakage current—that is, the small level of current that flows through the varistor even when the varistor is biased to behave as an open switch. The point labeled $V_N$ 1106 is the point along the curve that represents the switch voltage; in other words, the highest positive voltage value that corresponds to the switch region 1104 of the varistor. The point labeled $V_B$ 1107 represents the breakdown voltage of the varistor, where biasing voltages greater than $V_B$ cause the varistor to behave as a node. The point labeled negative $I_L$ 1108 represents the point along the curve that represents the negative leakage current. The point labeled $-V_N$ 1109 represents the point along the curve that represents negative switch voltage; in other words, the most negative voltage of the range representing the switch region 1104 of the varistor. The point labeled $-V_B$ 1110 represents the negative breakdown voltage.

The above-identified Dowling patents and application are at least directed to systems and devices for controlling corrosion comprising semiconductive coatings and a corrosive noise controlling system that includes a filter. In the case of the pending Dowling application, the corrosive noise controlling system includes an adjustable filter which may be adjusted based on feedback signals corresponding to the corrosive noise present in the coating.

The performance of the corrosive noise reducing system of the Dowling patents and application varies in accordance with the system's internal filter, which in its simplest form is essentially a capacitor. The Dowling patents and application also disclose combining the semiconductive coating with various passive and active filters. In the Dowling patents and application, the semiconductor coating acts somewhat as a resistor, which is in parallel with the system's internal filter. A summary of filter basics, such as how to implement a high-pass or low-pass filter, is found in *Microelectronics Circuits, Fourth Edition*, Sedra & Smith, Oxford University Press (1997), the entire contents of which are hereby incorporated by reference.

FIG. 5 is a graph of corrosion potential versus time with various filters. The horizontal axis 401 measures time in days while the vertical axis 402 represents potential relative to the semiconductor element measured in milli-volts. During an experiment directed to determining optimum filter characteristics for various corrosion environments, measurements were taken for seven systems at three points in time. The measured potential for each of seven filter configurations were recorded for those three samples and are indicated by various symbols listed in the legend. The graph displays the various results for each of the seven filters at the sampling points indicated from 410 through 430.

Electrochemical corrosion can De viewed schematically in terms of an equivalent circuit. Typically, the semiconductive material is doped with zinc. Thus, the simple equivalent circuit shown in FIG. 6 relates to the case of Zn oxidation. The anodic reaction occurs on the Zn and the cathodic on the ZnO. Note the Zr/ZnO boundary represents a varistor in the circuit. If the potential difference generated by the $Zn/O_2$ redox couple falls stably in the switch region, the Zn oxidation is inhibited (or passivated) by the high resistance of the boundary. However, over the past decade, it has been demonstrated that there are self-generated electrochemical potential fluctuations, "electrochemical noise" associated with corrosion. As a result, even though the $Zn/O_2$ potential may be in the switch region, there are likely to be fluctuations that drive the potential difference into the highly conductive region and allow electron flow and hence Zn oxidation.

The present inventors recognized that this is a way to passivate Zn so as to remove or filter the electrochemical noise. Removal of this electrochemical noise is via the filter, which in its simplest form, is a capacitor. The filtering effect maintains the potential across the Zn/ZnO boundary in the switch region and Zn oxidation is reduced and the life of the coating is increased. However, it is to be appreciated that the low pass filter may be augmented with passband (or notch) filters to selectively attenuate other frequency bands depending on the material being protected.

FIG. 6 shows an equivalent circuit diagram for the system of the Dowling patents and application. This figure abstracts the behavior of the system into a representative electrical circuit based on the electrochemical nature of metal corrosion processes. Specifically, corrosion can be modeled as a fluctuating voltage source, the metal's inherent resistance can be represented, the anti-corrosion coating can be modeled as a varistor, and the noise filter can be modeled as a capacitor. By placing these modeled elements in a circuit diagram, the noise and filter components of Dowling can be more clearly conceptualized using electrical circuit analysis.

Within the representational circuit is a solution resistance 801 which represents the inherent resistance of the system in series with the galvanic electrode potential at the anode 802 which corresponds to the ionization process of zinc and the galvanic electrode potential at the cathode 803 which corresponds to the chemical process producing water. Also present and connected in series with the circuit are two noise sources 804, one of which is interposed between the galvanic electrode potential of the anode and the Faradaic impedance of the anode 805 and another interposed between the galvanic electrode potential at the cathode 803 and the Faradaic impedance of the cathode 806 placed in series between the Faradaic impedances of the anode and cathode are the zinc oxide varistor 807 and the noise filter 808. The varistor and noise filter act to reduce the occurrence of voltage fluctuations which can induce corrosion. The noise filter 808 may be active, passive, or both and, by selecting a node in the circuit to be designated common potential 810, the filter 808 can attenuate high frequencies in the circuit due to the corrosion noise.

The substrate on which the semiconductive layer is placed may be conductive or non-conductive. Conductive substrates can be metallic or non-metallic. Non-conductive substrates can be any material that acts as an insulator, such as a silicon wafer or other non-metal substrate. The production of such non-conductive or conductive substrates in the art of semiconductor chip manufacture is well known to one of ordinary skill in the art.

The corrosion noise reducing system of the Dowling patents and application provides a means for preventing corrosion of a conductive structure susceptible to corrosion by coating the conductive structure with a semiconductive coating and connecting the resulting coated structure to a passive or active electronic filter so as to minimize the corrosive noise in the coating. The electronic filter has a filter response such that it attenuates the high frequency spectral content of the corrosion noise. This is achieved by connecting a filter, having an impedance characteristic in the form of a low pass filter (possibly augmented by notch filters) across the material being protected. Furthermore, depending on the material and the application, possibly other frequency bands may selectively be attenuated so as to reduce corrosive effects. The filter can be a passive filter or an active filter. In either case, the filter attenuates the higher frequency voltage fluctuations. The junctions present in the semiconductor coating then maintain a reverse bias. The time-averaged electron flow from the anodic to the cathodic domains in the semiconductive coating is then reduced and the coating is effectively passivated.

With the filter engaged to the circuit equivalent of the corrosion process, the noise signal can be dissipated as shown in FIG. 7, where a metal surface 501 is covered by a protective coating 510 connected to a filter 508 so the metal has a significantly attenuated noise electrostatic 502. The filter 508 acts either as a standalone low pass filter or possibly in combination with filters having impedances in the form of bandpass and/or notch filters to reduce the high frequency corrosive noise 522. Effectively, the filter dissipates the energy associated with the higher frequencies in the electrochemical noise signal. Attenuation of the high frequency spectral contents of the electrochemical noise will significantly reduce me corrosion process by inhibiting the voltage fluctuations across the varistor outside the switch voltage (Vn)

SUMMARY OF THE INVENTION

Accordingly, one object of the present invention is to provide a system for monitoring a parameter associated with space weather effects and controlling corrosion of a structure caused by such effects.

Another object of the invention is to provide a corrosion noise reducing system having an Electronic Control Unit (ECU), a controllable filter (optionally including a fixed, passive filter), and a semiconductive coating on a substrate so as to provide a low resistance path to ground for corrosion noise caused by space weather effects.

A further object of the present invention is to provide a system and method for protecting pipelines from the corrosion effects of space weather.

These and other objects are achieved by the inventive system and method described herein. The present inventors recognized that a corrosion noise reducing system having a semiconductive coating on a substrate can be optimally operated with an Electronic Control Unit ECU) and a controllable filter so as to control filter operations and voltage fluctuations in the conductive structure on which the semiconductive coating is placed. These benefits are achieved via a method for monitoring space weather effects and controlling a filter, that optionally, although is not limited to, using adjustable filter components and/or fixed components based on a set of predetermined and/or measured parameters in response to the space weather effects, thereby controlling the rate at which space weather induced corrosion of the structure occurs. Previous patents such as the Riffe and Dowling patents discussed above, covered monitoring of parameters such as the temperature, salinity/water purity, humidity, age, short term duty cycle, long term duty cycle, immediate speed of vessel, vessel speed history, immediate geographic location, geographic location history, age of coating, coating deterioration, thickness of coating, surface area coated, and shape of coated area. The present invention extends these parameters to those specifically related to space weather, including but not limited to, early warning data from observational satellites (e.g. The Solar and Heliospheric Observatory (SOHO), or Advanced Coronal Explorer (ACE) etc), spikes in electromagnetic activity, auroral zone electric currents, changes in the structure's potential relative to ground, geomagnetic induced currents and telluric currents.

BRIEF DESCRIPTION OF THE FIGURES

A more complete appreciation of the invention and many of the attendant advantages thereof will be readily obtained as the same becomes better understood by reference to the following detailed description when considered in connection with the accompanying Figures, wherein.

DETAILED DESCRIPTION OF THE PREFERRED EMBODIMENTS

The present invention provides a corrosion noise reducing system having an Electronic Control Unit (ECU), a controllable filter, and a semiconductive coating on a substrate.

The present invention is aimed at the prevention of corrosion in structures susceptible to space weather effects, including but not limited to geomagnetically induced currents (GIC) or Telluric Currents, most notably large ground based structures, such as bridges; pipelines; rail lines and structures; steel structures; and storage tanks, although it may be used with other objects as well.

As determined by the present inventors, a controllable filter and controller may be used in a corrosive noise reducing system where the controller dynamically adjusts the filter characteristics of the corrosive noise reducing system by taking into account various parameters related to space weather effects so as to minimize or eliminate the corrosive effects of such space weather. Parameters that may be monitored in accordance with the present invention are those relating to space weather effects that can result in corrosion of the structure being protected, including but not limited to, early warning data from observational satellites (SOHO, ACE etc), spikes in electromagnetic activity, auroral zone electric currents, changes in the structure's potential relative to ground, geomagnetic induced currents and telluric currents. A non-limiting list of examples of other parameters that can be monitored in addition to those related to space weather effects (in order to prevent simultaneously prevent corrosion caused by other sources), includes one or more of: temperature, salinity/water purity, humidity, age, short term, duty cycle, long term duty cycle, immediate speed of vessel, vessel speed history, immediate geographic location, geographic location history, age of coating, thickness of coating, deterioration of the coating, surface area coated, and shape of coated area. In view of the discovery that it is possible to minimize and/or eliminate the corrosion effects of space weather on a structure susceptible to such effects, the present inventors identify and describe herein, systems, devices, algorithms, methods, and computer program products for controlling filter operations associated with an anti-corrosion semiconductive coating and a corrosive noise reducing system.

Figure 1:
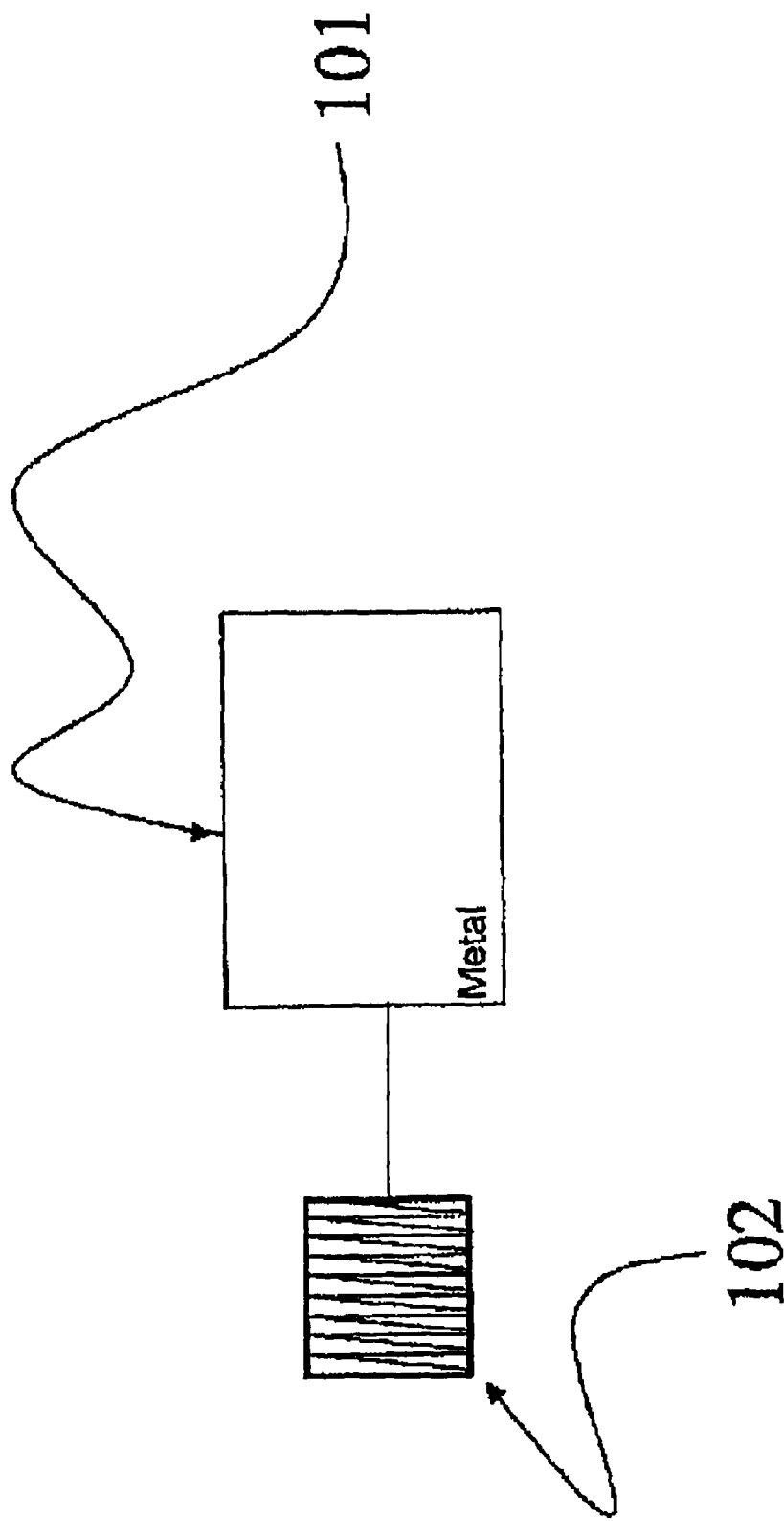
FIG. 1 is a representation of corrosion noise in unprotected metal.
Figure 2:
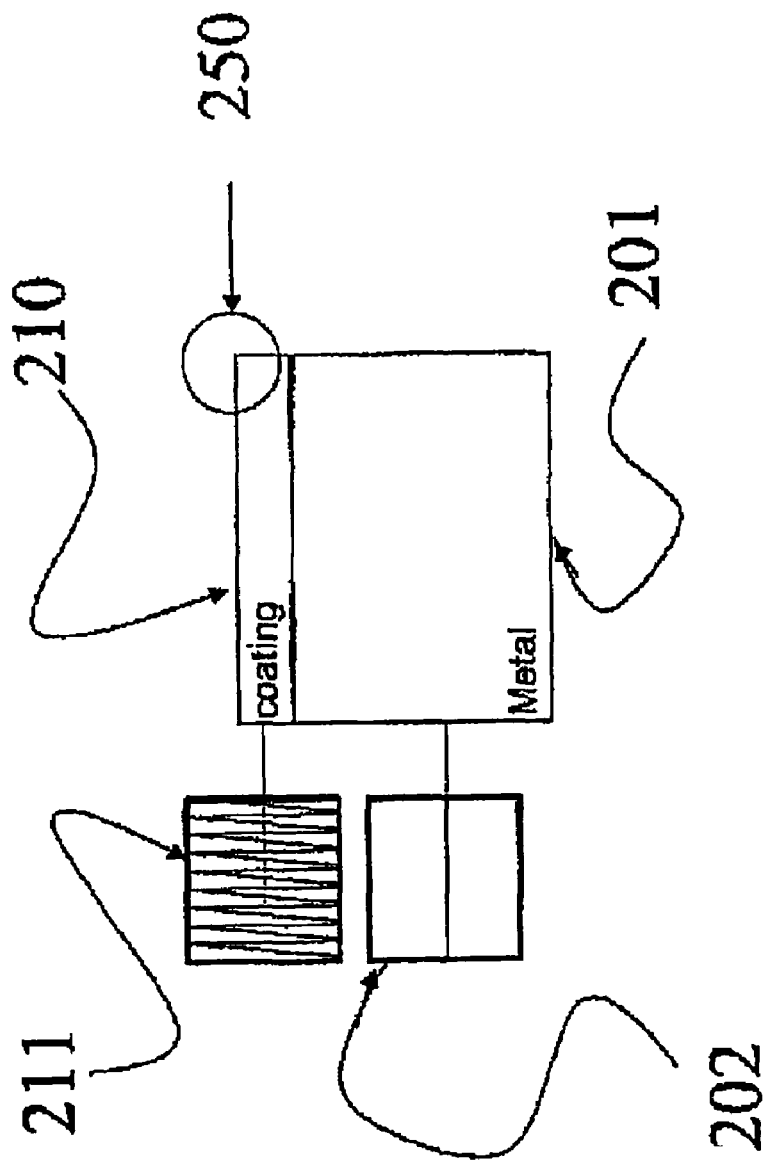
FIG. 2 is a representation of corrosion noise in protected metal and in a semiconductor coating.
Figure 3:
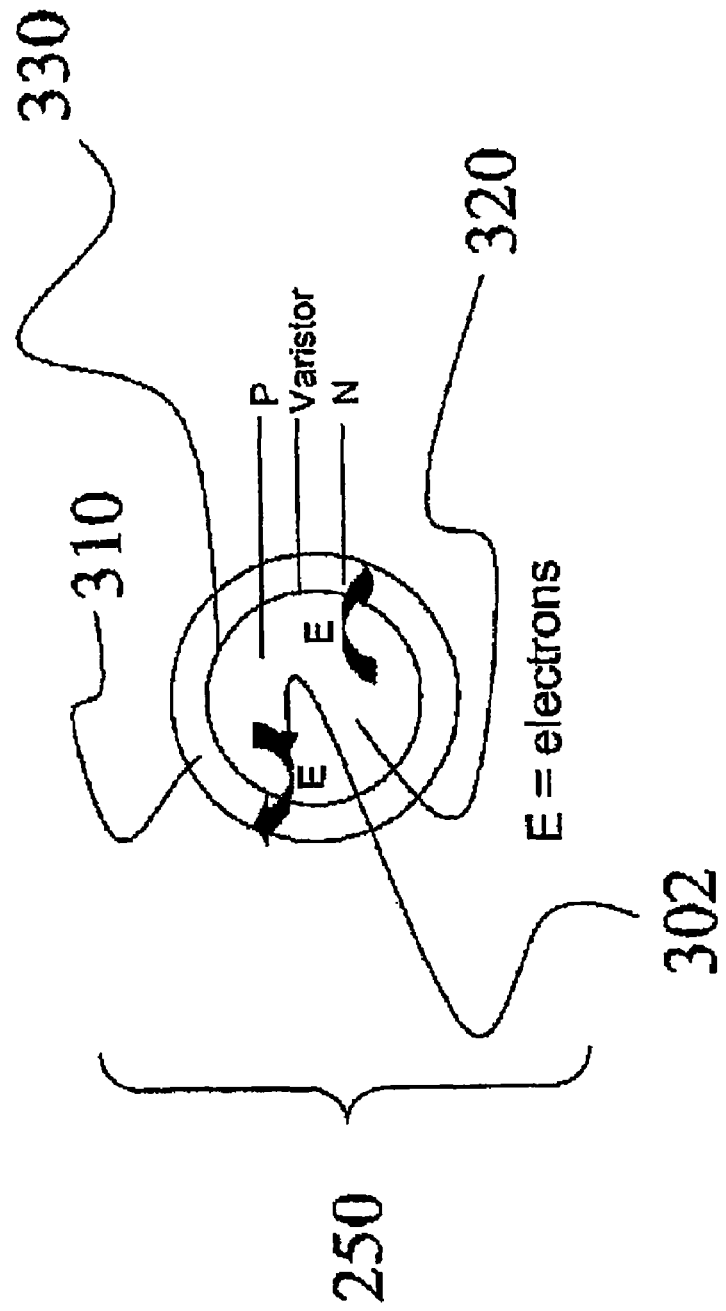
FIG. 3 is a representation of current flow between a metal and a semiconductor protective coating.
Figure 4:
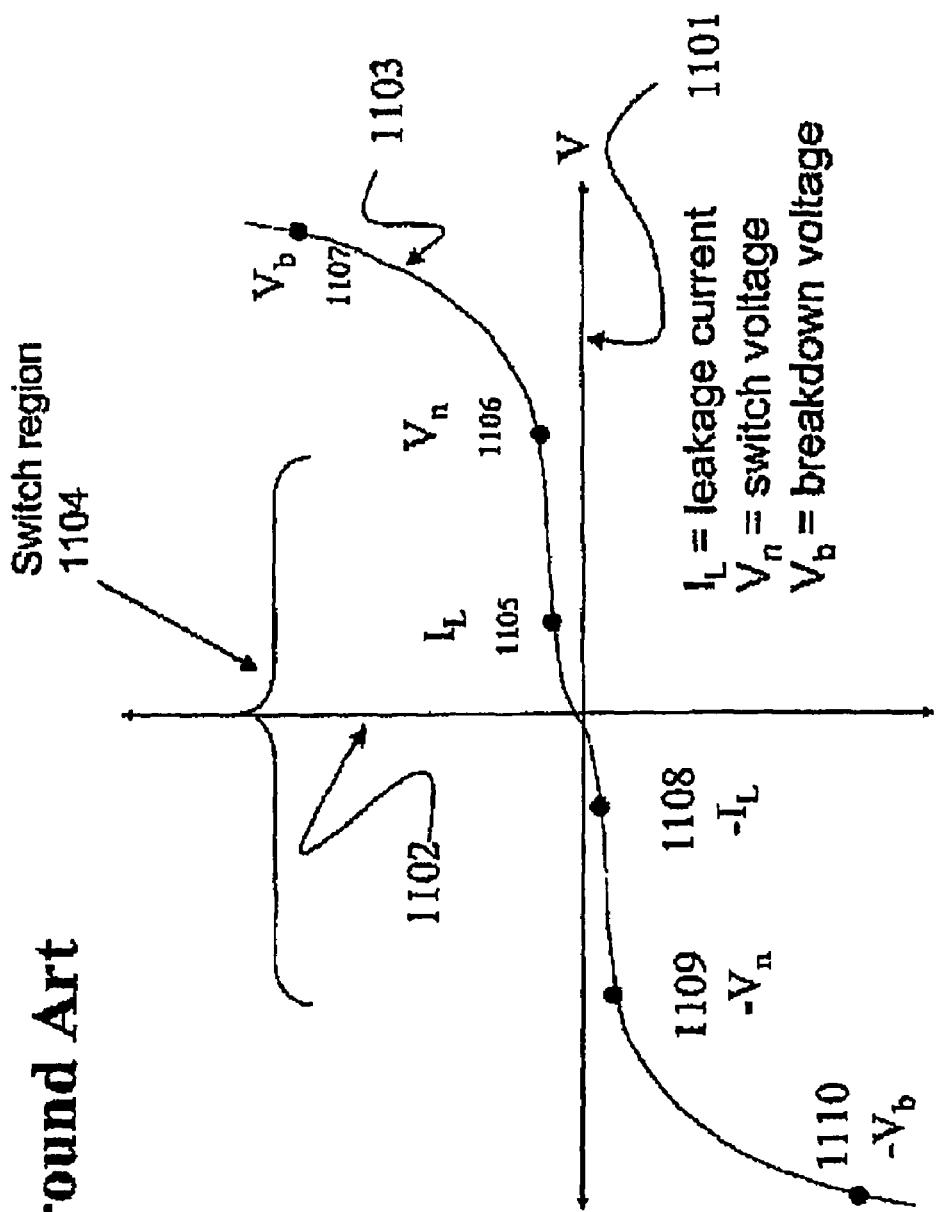
FIG. 4 is a graph of varistor-like operations between a metal and a semiconductor protective coating.
Figure 5:
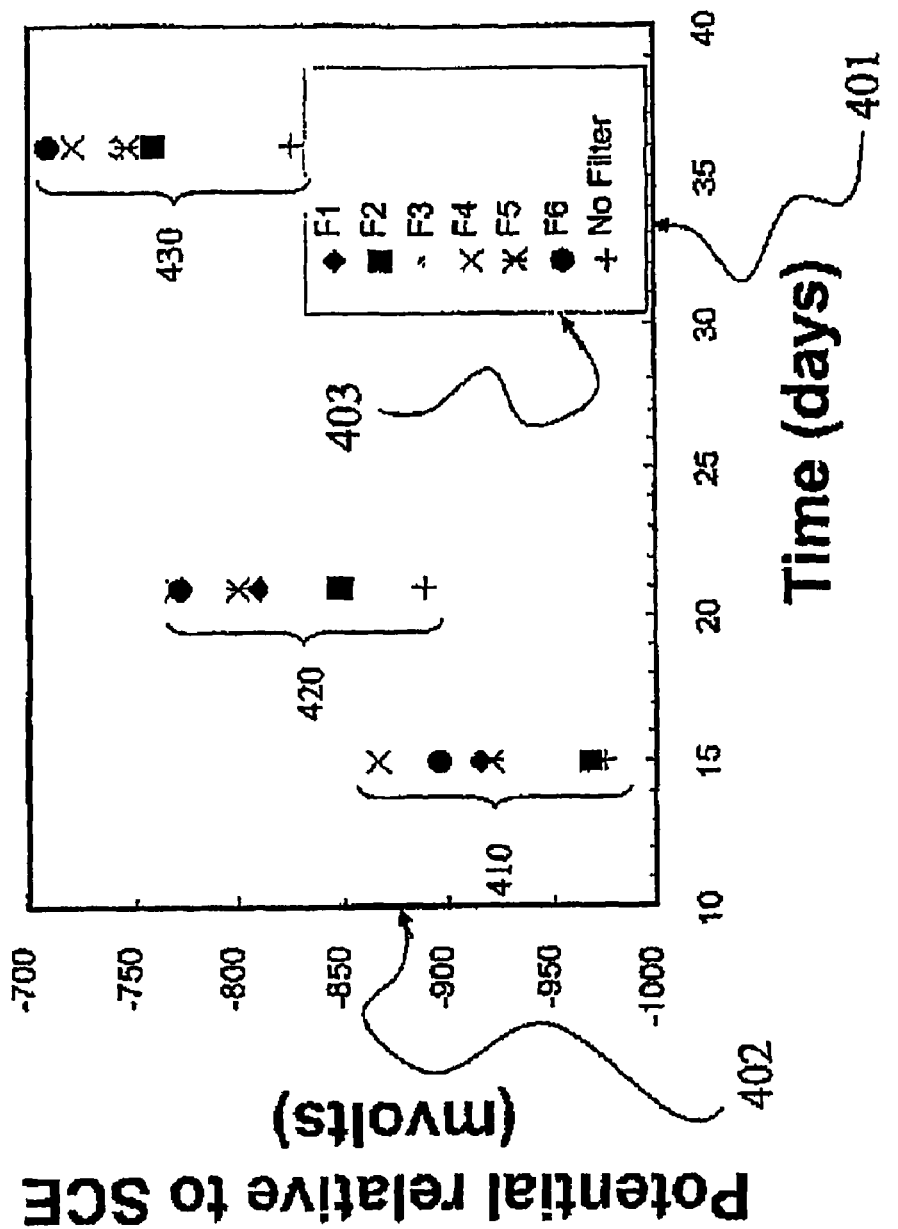
FIG. 5 is a graph of corrosion noise vs. time for various filters.
Figure 6:
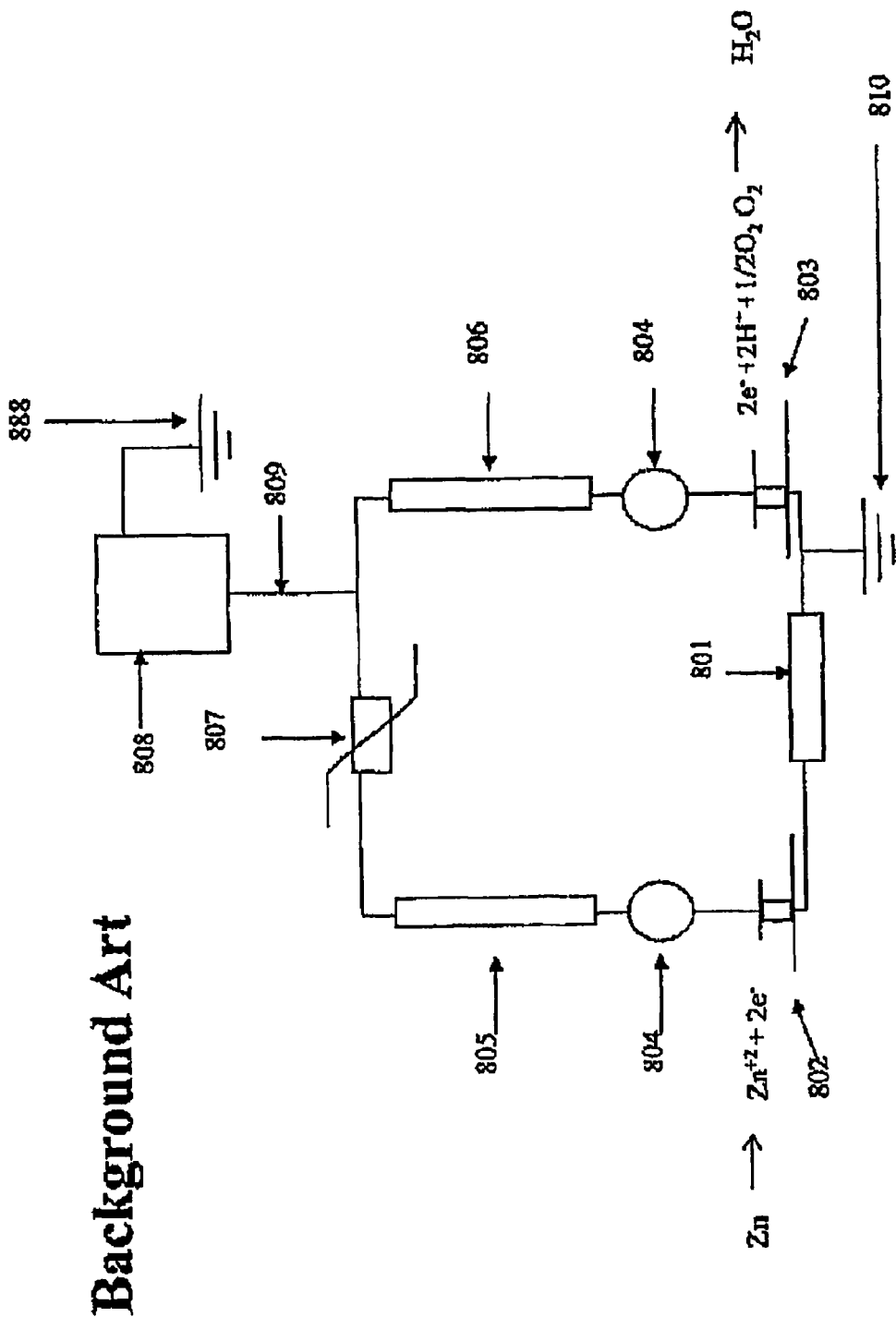
FIG. 6 is a circuit diagram of a corrosion noise reducing system without an Electronic Control Unit (ECU)
Figure 8:
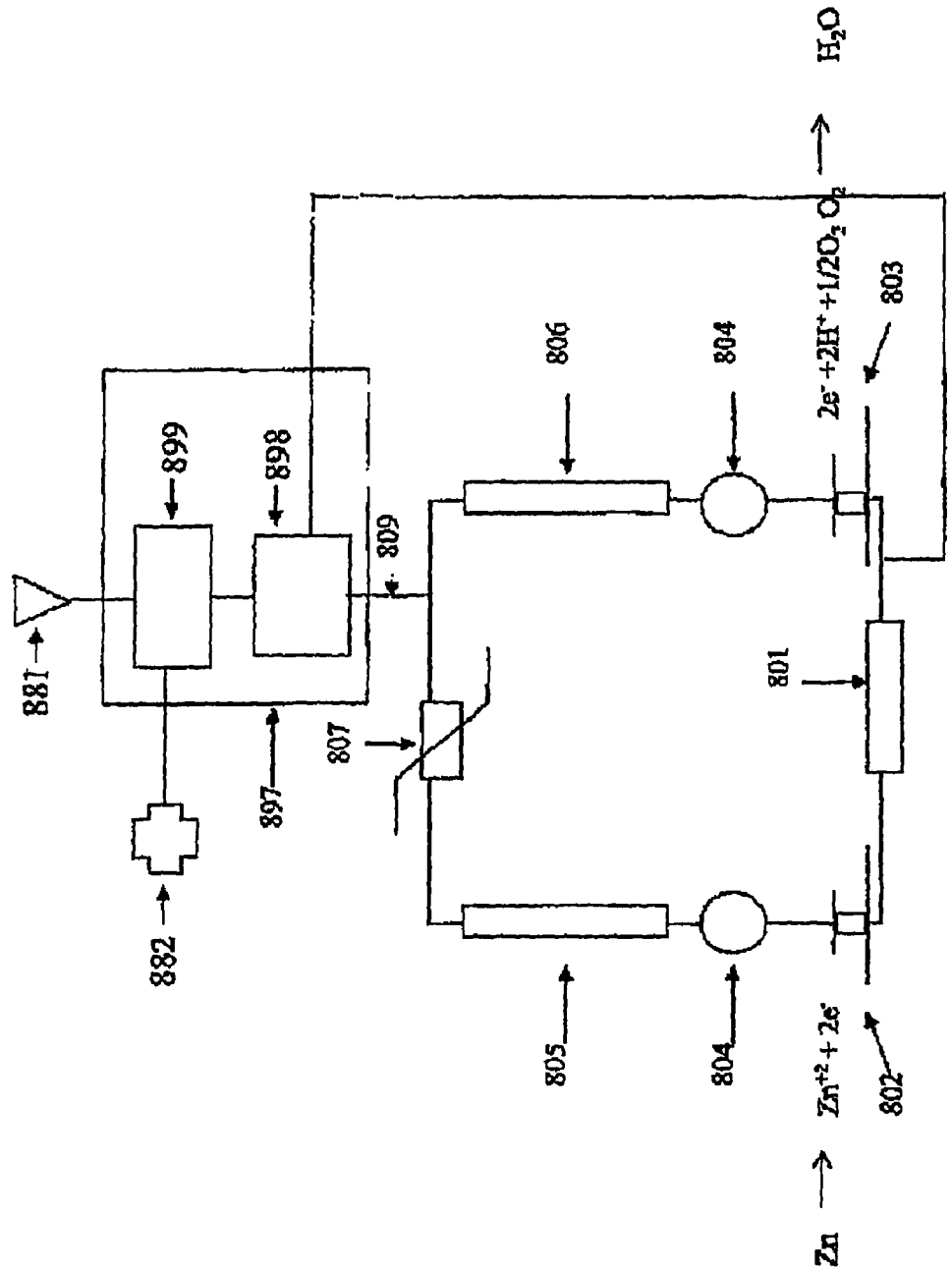
FIG. 8 is a circuit diagram of an ECU containing a controllable corrosion noise filter and ECU control circuit.

FIG. 8 is a circuit diagram of one embodiment of the present invention where components similar to those found in FIG. 6 retain their previous indicia. As shown, the ECU 897 contains a controllable filter 898 and an ECU control circuit 899. The ECU 897 may optionally be connected to one or more local sensors 882, and/or be connected to, and/or contain, an antenna (e.g., for use in wireless communication) 881 or other mechanism for achieving wireless communication, such as with optical transceivers. The ECU may also access data stored in a local data archive (not shown) or in a remote archive accessible via the antenna 881, other wireless communication mechanism or even wired connection, such as a network. The ECU control circuit 899 is configured to change a filter characteristic of the controllable filter 898, such that the frequency-dependent impedance of the controllable filter 898 is changed depending on the mode of the operation of the ECU control circuit 899. It is also to be appreciated that the present invention is not limited to this specific configuration, as will be appreciated by one of ordinary skill in the control system art.

Figure 9:
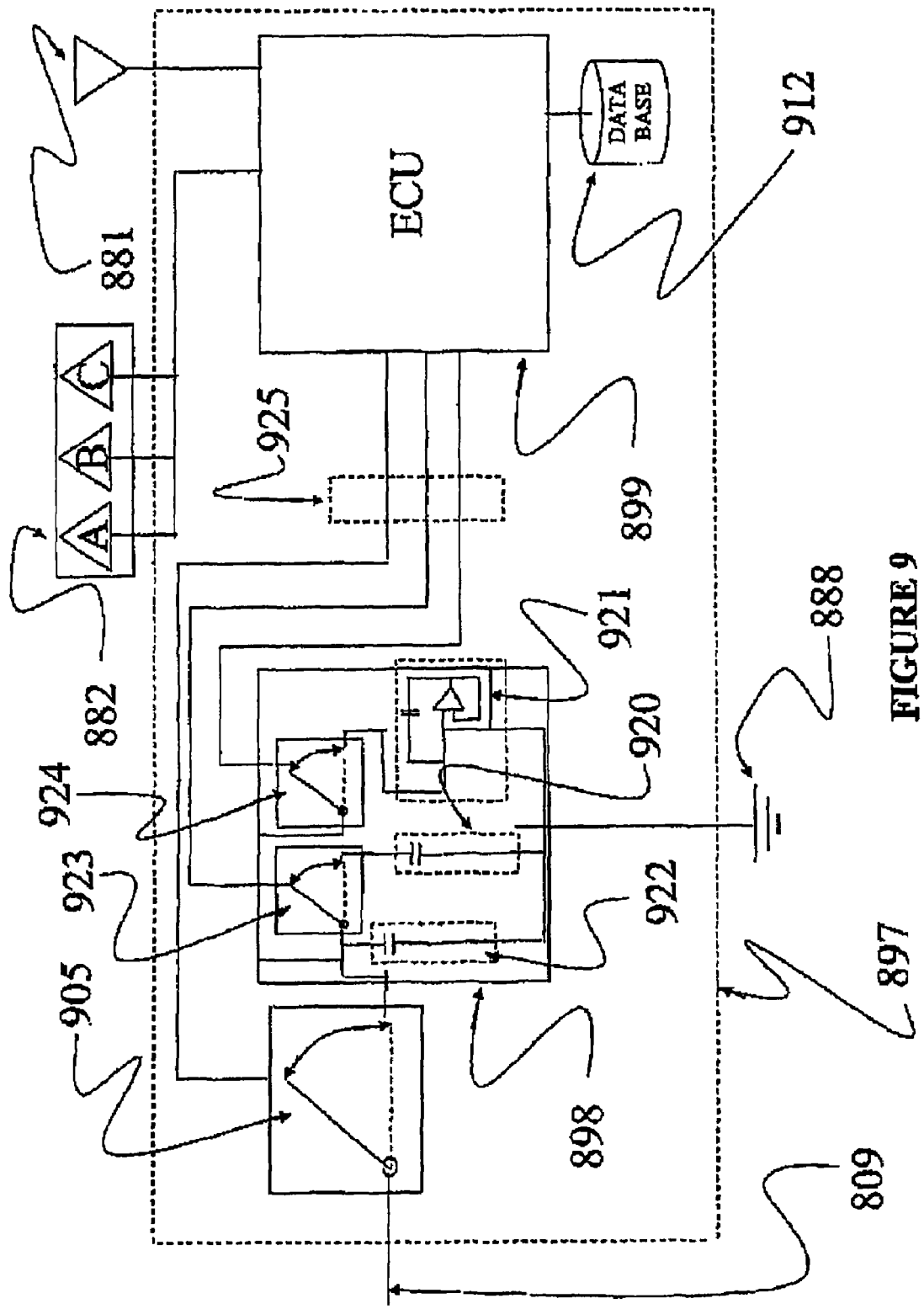
FIG. 9 is a block diagram of an ECU containing a controllable corrosion noise filter and ECU control circuit.

FIG. 9 is a block diagram of an embodiment of the present invention and includes an ECU 897 containing a controllable filter 898 and an ECU control circuit 899. While a filter composed of a single capacitor is shown, other circuit components may be used to implement various filters (e.g., having impedances in the form of notch filters) augmenting a low pass filter impedance characteristic. Schematically, the combination of the controllable filter 898 and an ECU control circuit 899 is represented as a single system 897 connected to the other elements of the corrosion system by a conductive link 809. The controllable filter 898 may include any configuration of various filters (e.g., filters having impedances in the form of low pass, notch filters, bandpass, etc.) configured to attenuate targeted high frequency signals corresponding to corrosion noise. The controllable filter 898 may optionally be disconnected from the system using an electronically controllable switch 905 that may be controlled by the ECU control circuit 899 or by other means such as a manual toggle switch, patch panel or other device that can automatically or manually, electrically insert and/or remove components from a circuit. The controllable filter 898 may be controlled by the ECU control circuit 899 by way of the control lines 925, which open or close switches 923 and 924 connecting a plurality of supplemental filters 920 and 921 (this may optionally include a switchable filter bank, which together can apply different filter characteristics to corrosion noise). It is also a feature of the invention that the ECU control circuit 899 electronically controls/adjusts the filter characteristics of the controllable filter 898 through adjustable circuit elements, which may optionally be voltage controlled resistors or switched variable capacitances. The ECU 950 may be connected to a wireless receiver/transmitter 881 so as to receive and/or transmit one or more control signals with a remote ECU control location (optionally thru a wireless electromagnetic and/or optical link). The ECU control circuit 899 may be connected to one or more local sensors 882, each configured to monitor one or more parameters related to the presence and/or effect of GIC or Telluric Currents, used by the ECU control circuit 899. Information received from the wireless receiver 881 and/or local sensors 882 may be used by the ECU control circuit 899 to adjust the controllable filter 898 or disconnect it entirely. Additionally, the ECU control circuit 899 may interface with a local and/or remote database 912 so as to process the information received from the wireless receiver/transmitter 881 and/or local sensors 882.

The effectiveness of the semiconductive coating can be optimized through the use of filters with specific frequency response characteristics selected for the needs of a particular application, as well as the use of adaptive active filters, monitoring the "electrochemical noise" of the protected object and adjusting its response accordingly. Specific filters are configured and operated so as to excise corrosion noise thereby resulting in a smaller amplitude, low frequency voltage across the semiconductor coating. One or more filters are configured and attached to the coating in one or more places along protected structure so as to provide a low resistance path to ground for 'high frequency' corrosion currents formed in and on the semiconductor coating. 'High frequency' is a term used herein to describe non-DC components of corrosion noise. In practice for typical structures, the high frequency component of corrosion noise is in the 10's of Hertz and higher. High frequency, as used herein, may also include the transition band between DC and 10 Hz for example, and thus includes frequencies at 1-10 Hz for example. Thus, cut off (or 3 dB points) of filter characteristics for controllable filters employed by the present invention are typically, although need not be limited to, 1 to 10 Hz. Depending on the nature of the corrosion noise, the filter characteristics may be adapted to suppress even lower frequencies, such as ¼, or ½ Hz and above, or even at one or more particular frequency bands (which may be notched out with one or more filters having impedances in the form of a notch filter).

Figure 10A:
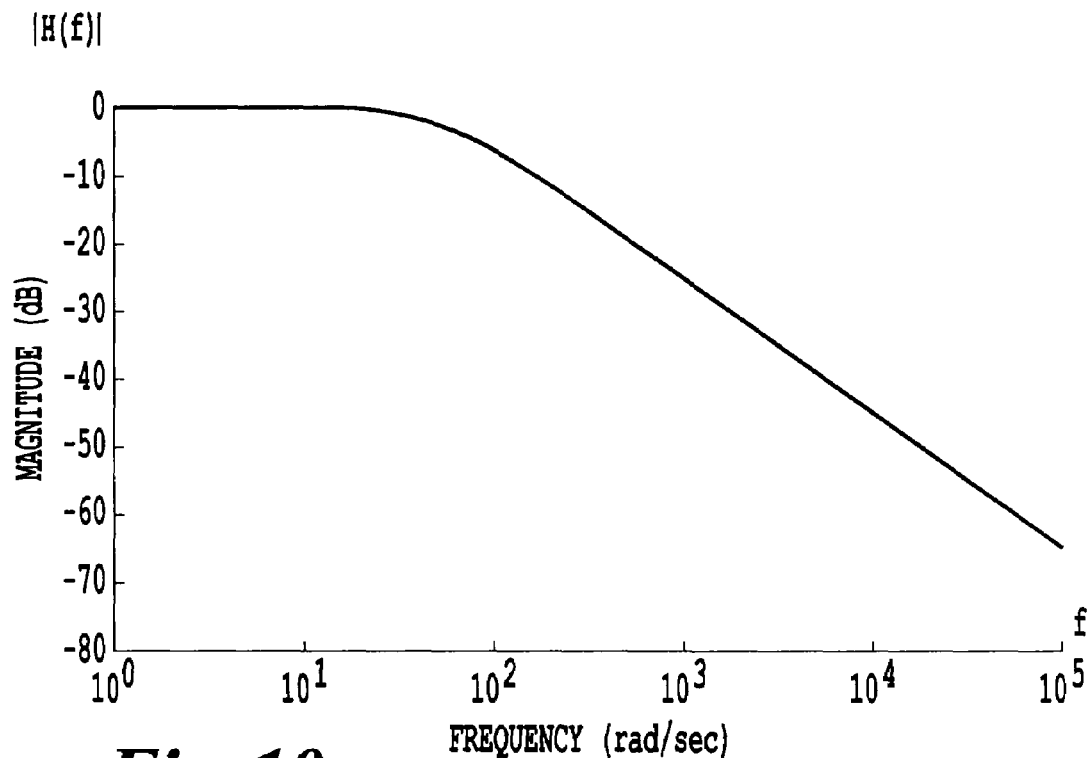
FIGS. 10A and 10B are amplitude and phase response curves, respectively, for a corrosion noise bandpass filter of one embodiment of the present invention.
Figure 10B:
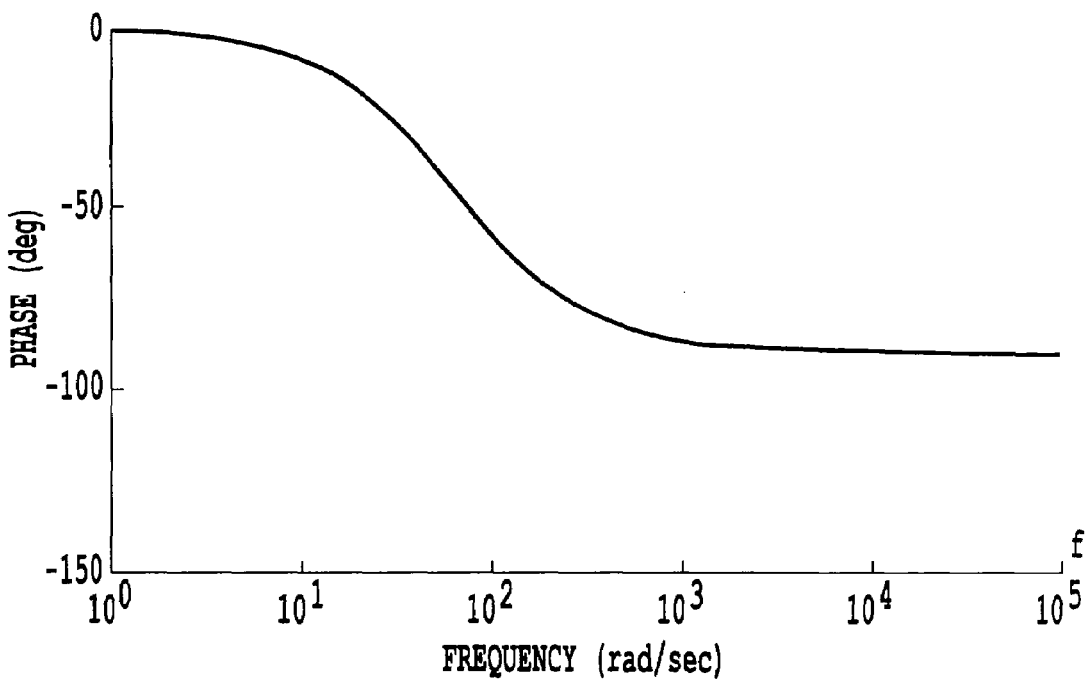

FIGS. 10A and 10B are amplitude and phase response curves, respectively, for impedance of an exemplary corrosion noise lowpass filter of one embodiment of the present invention. These Bode plots show a 3 dB point at about 10 Hz. Alternatively, filters having low pass impedance characteristic with 3 dB points of 5 Hz, 15 Hz, 25 Hz, 100 Hz or other values may be used depending on the protected material so long as significant non-DC components of spectral energy are removed from the protected structure so that voltage fluctuations outside the switch voltage range are significantly reduced. One or more of such filters having low pass impedance characteristic may be electrically connected to the protected structure at one or more locations to remove the unwanted corrosion noise energy while reducing or preventing any corrosion noise currents across the protected structure. One or more of these low pass filters may be controlled by the Electronic Control Unit in terms of filter frequency response and/or physical connection. Alternatively, higher-order filters may be used to change the roll-off rate of the characteristic curve, thereby further suppressing high frequency energy at frequencies closer to the 3 dB point. This electronic filter provides a path to ground for the electrochemical noise signal that induces loss of electrons and therefore corrosion. To effectively reduce corrosive effects, smaller impedances at lower frequencies need to be achieved (i.e., by increasing the size of the capacitor, if the system filter is purely a capacitor).

Figure 11A:
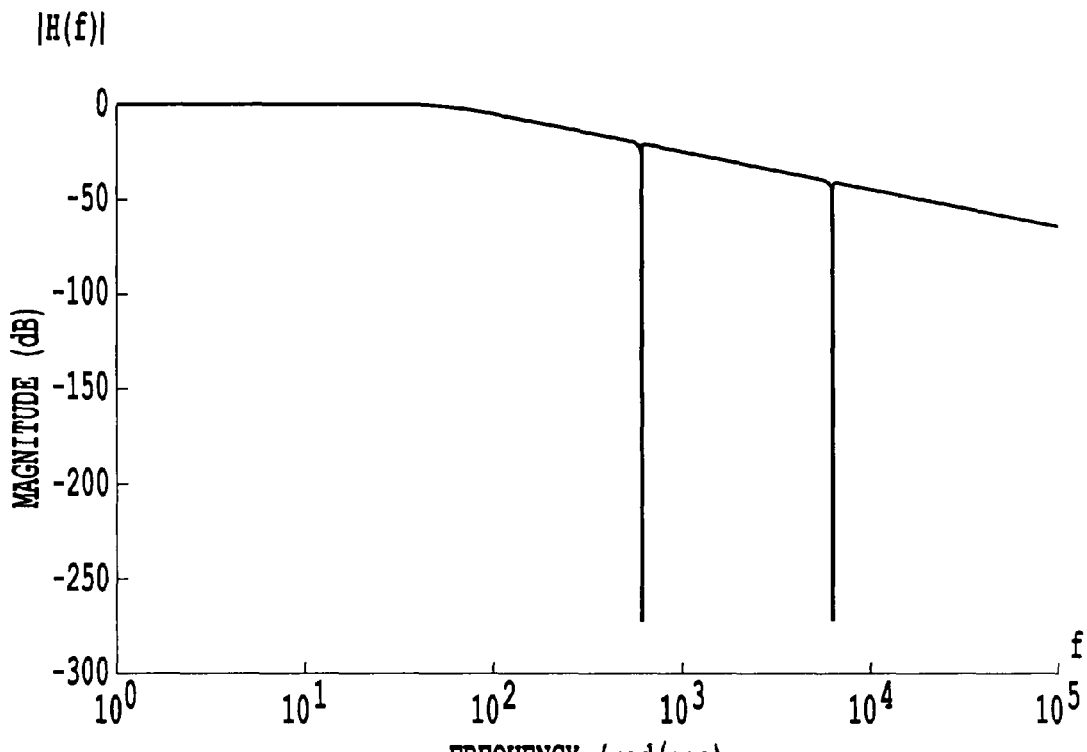
FIGS. 11A and 11B are amplitude and phase response curves, respectively, for a corrosion noise notch filter of one embodiment of the present invention.
Figure 11B:
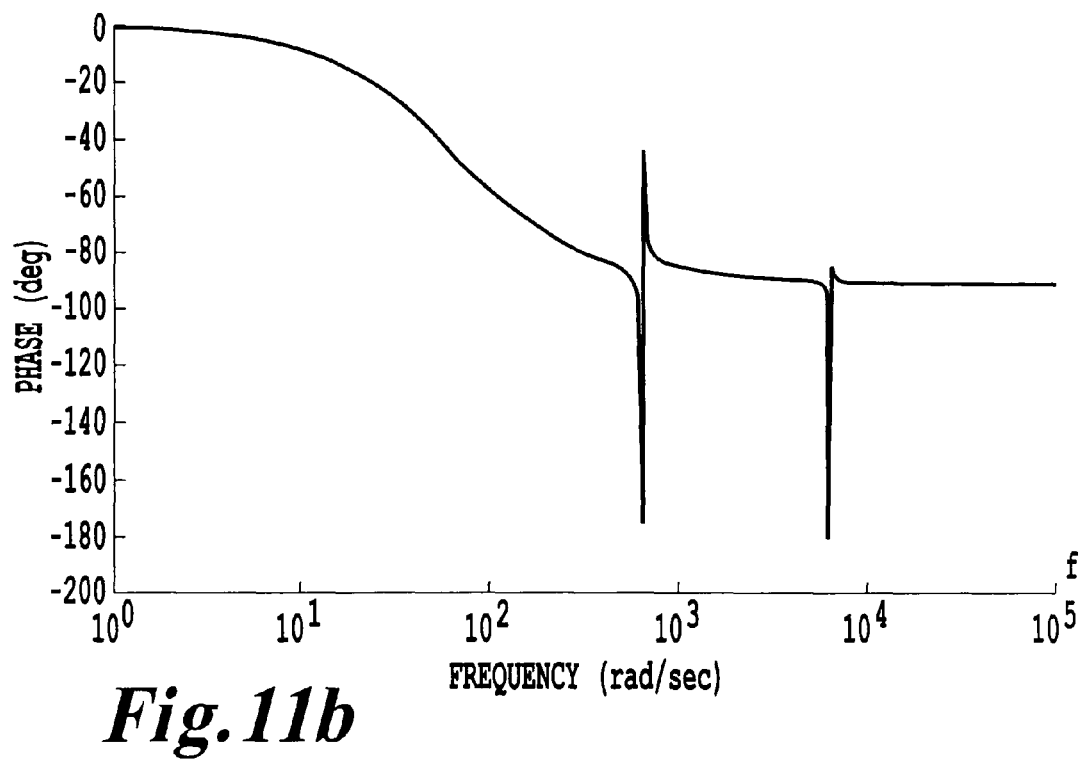

FIGS. 11A and 11B are amplitude and phase response curves, respectively, for a corrosion noise filter having low pass impedance characteristic augmented by notch filters of one embodiment of the present invention. As shown, multiple (or just one) notches in the impedance of the filter may be used in conjunction with the low pass impedance characteristic of FIGS. 10A and 10B to excise one or more corrosion noise spectral content. One or more such filters may be electrically connected to the protected structure at one or more locations to remove corrosion noise energy peaks while reducing or preventing any corrosion noise currents across the protected structure. One or more of these notch filters may be controlled by the Electronic Control Unit in terms of frequency response and/or physical connection. Alternatively, higher-order filters may be used.

The control of the one or more filters with low pass and/or notch impedance characteristics, and higher-order filter exercised by the Electronic Control Unit may be based on one or more corrosion noise measurements provided by one or more corrosion noise sensors monitoring the protected structure.

For all combinations of filters and filter connections, the effectiveness of the semiconductive coating can be further optimized over the life of the object being protected by configuring the ECU to adjust its filter operations in response not only to the effects of GIC or Telluric Currents, but also adjusting the filter operations in response to a series of other measured and/or predetermined parameters that are related to corrosion to include one or more of: measured corrosion noise, temperature, salinity, humidity, age of coating, surface area coated, thickness of coating, deterioration of coating, shape of coated area, location of vessel/object coated, vessel moving or stationary, history of operation.

Figure 12:
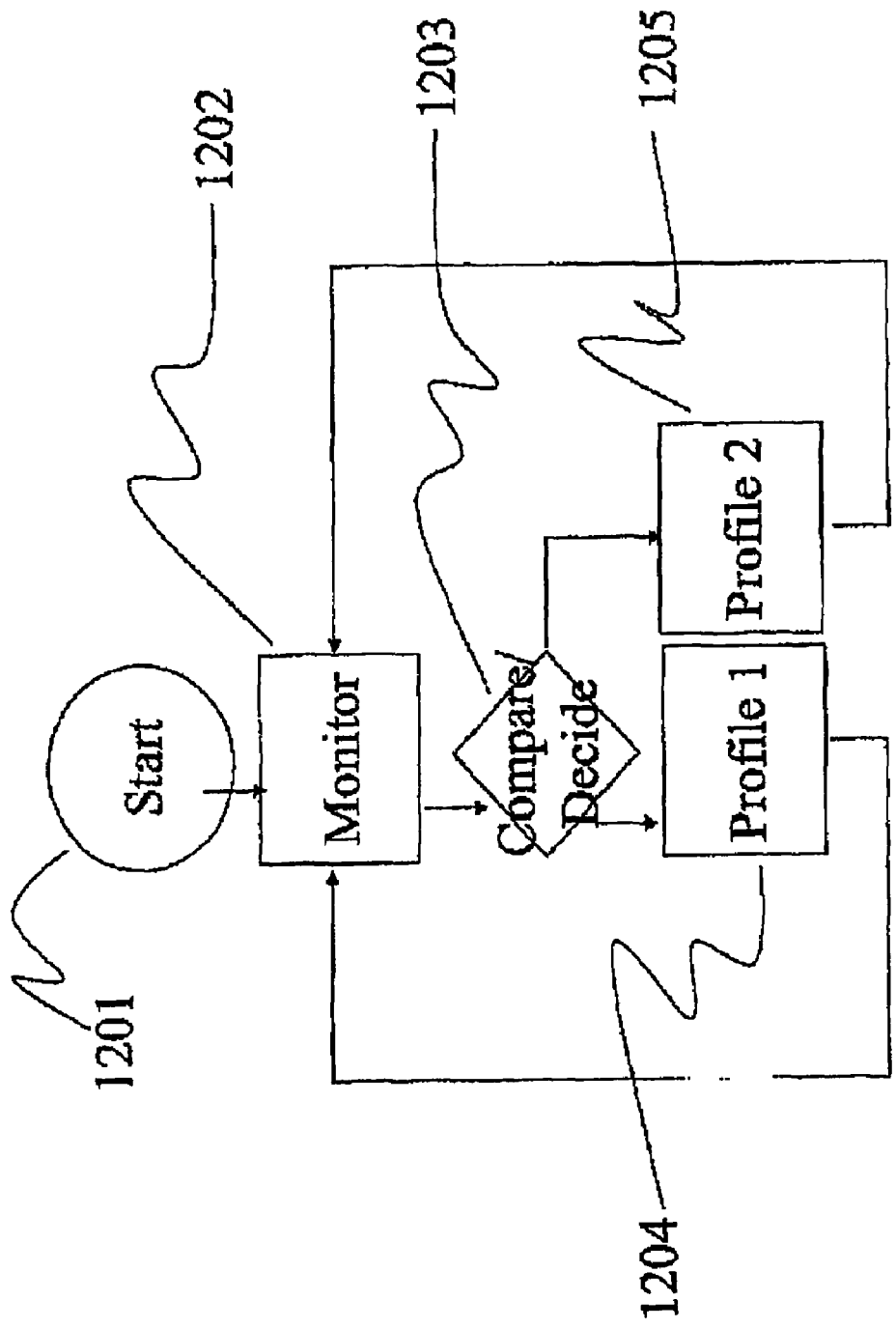
FIG. 12 is a flow chart of method of reducing corrosion noise with an ECU.

FIG. 12 is a flowchart representing a non-limiting exemplary process used in an embodiment of the present invention. The process represented by this flowchart may be used in the ECU to control the behavior of the filter in order to optimize the balance between anti-corrosive effects and anti-fouling effects. In the process, the system progresses from a start step 1201 to a monitoring phase step 1202 in which inputs may be taken from various monitors and sensors, including salinity, position of the system, system history or other factors. The system then compares the monitor values and decides in step 1203 which of two predetermined operating profiles the filter should adopt, steps 1204 and 1205, respectively. When this action is complete, the system returns to the monitoring phase step 1202 and repeats the process. In this embodiment, two filter profiles are shown. In other embodiments, three or more profiles may be selected.

The control parameter measurement and exploitation aspects of the present invention are used to fine-tune the performance of the system for specific applications. Based on the control parameters, the requisite filter properties in the system can be determined and can be improved for consistent corrosion prevention over the entire surface of the structure, even in very large structures, such as pipelines or large span bridges. In the present invention, the voltage fluctuations between the coated surface and a low-noise high impedance reference electrode are monitored for when the voltage peak exceeds a predetermined threshold, a predetermined number of times, per time interval (e.g., 3-tens per second), and/or a heightened noise environment is detected. This threshold detection technique is one way to measure the standard deviation of the noise, which in turn is a measure of noise power. Alternatively, an FFT, or other signal processing technique, could be used to measure noise power as a function of frequency. The frequency content of the noise signal and its power content may be measured by such measuring devices such as a spectrum analyzer or through digitization of signal and performing various signal processing techniques in a real-time embedded processor in the ECU. In addition, other parameters may be used (individually or in combination) to manually or automatically adjust filter characteristics and/or filter duty (i.e., on/off) cycle. These include, but are not limited to, the previously identified parameters of: measured corrosion noise, temperature, salinity, humidity, age of coating, surface area coated, thickness of coating, deterioration of coating, shape of coated area, location of vessel/object coated (e.g., North Sea vs. South China Sea), vessel moving or stationary, history of operation (e.g., ratio of time stationary vs. moving).

In another embodiment, the ECU is connected to a Global Positioning Satellite subsystem through an industry standard or proprietary bus such as VMEbus or through a wireless communication mechanism. By monitoring the geographic location of the system, the ECU adjusts the effective values of the corrosion noise filter characteristics according to predetermined criteria taking into account what is known about the effects of space weather affecting corrosion that are associated with the system's geographic location.

Figure 7:
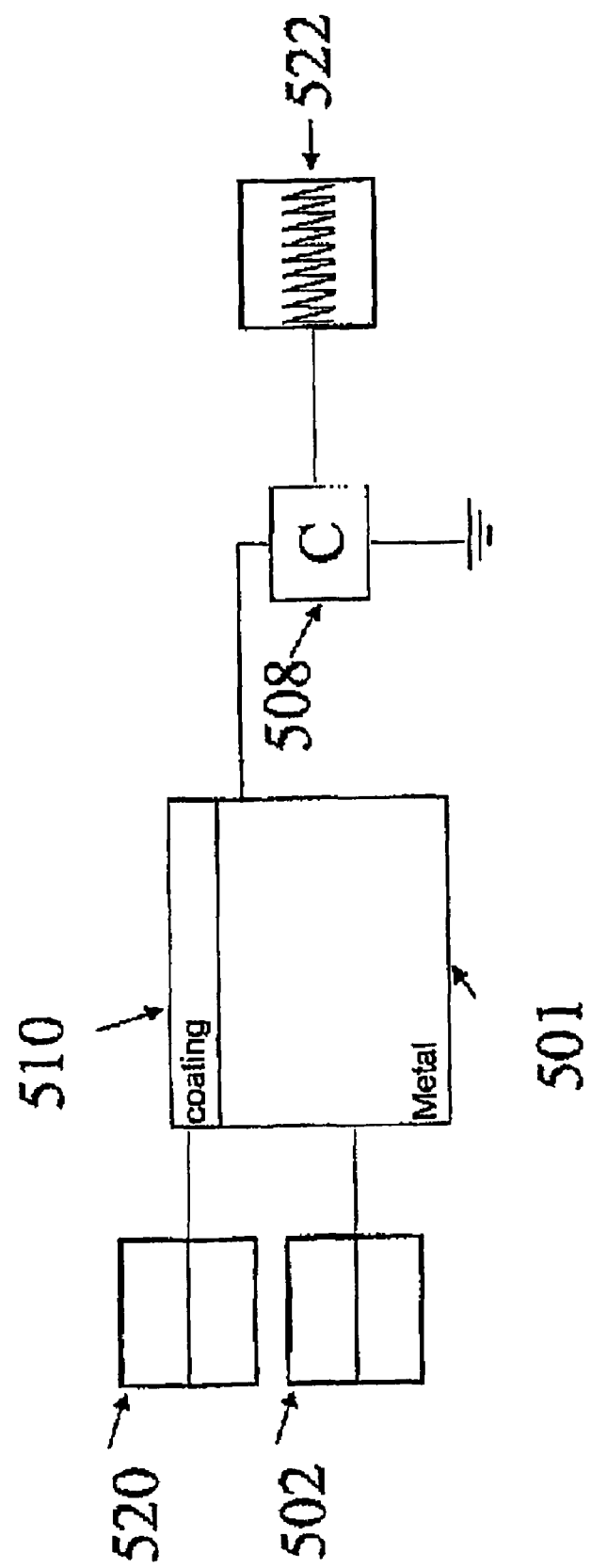
FIG. 7 is a block diagram of a corrosion noise reducing system including metal, a semiconductor protective coating, a filter, and component noise characteristics.
Figure 13:
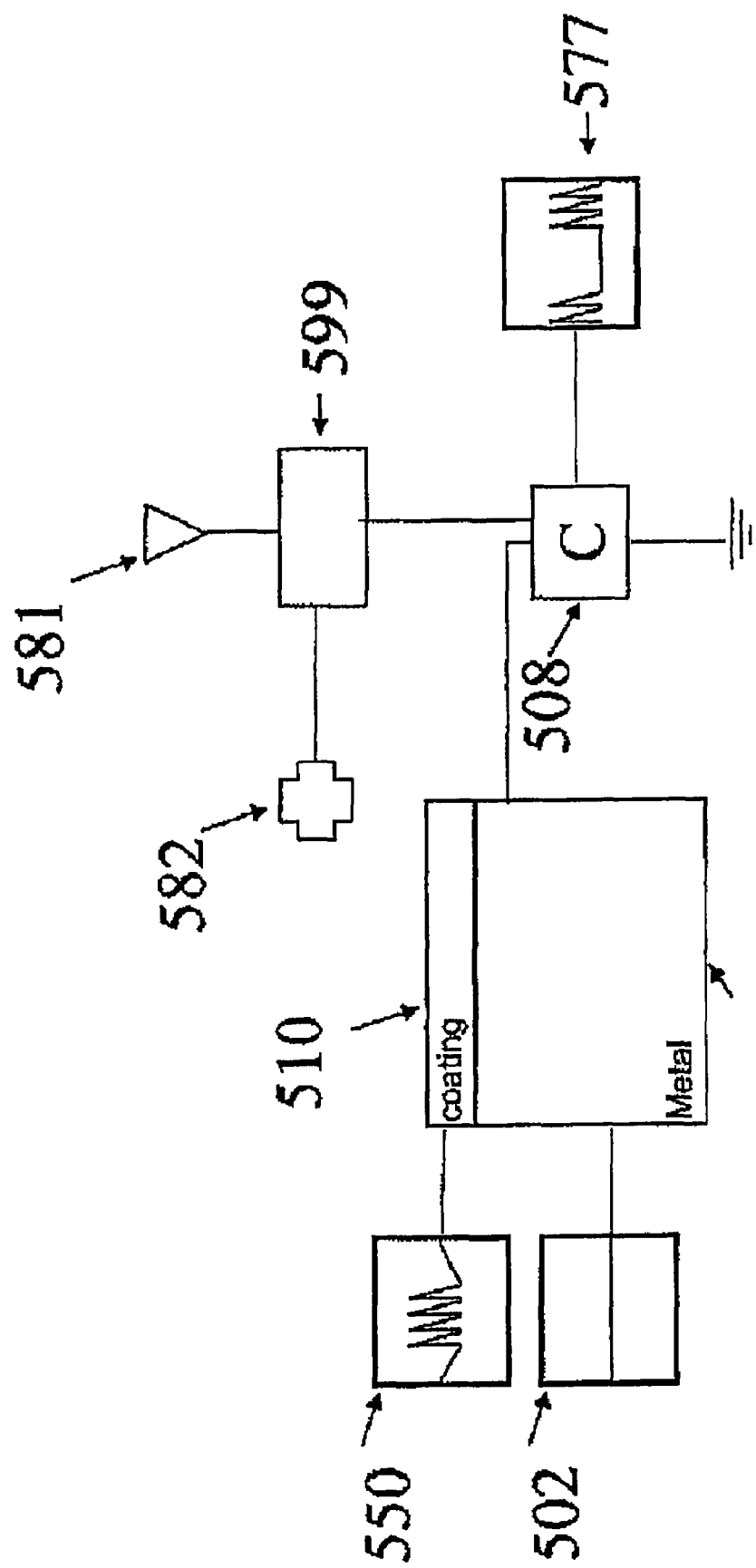
FIG. 13 is a block diagram of a corrosion noise reducing system including metal, a semiconductor protective coating, a filter, an ECU, and component noise characteristics.

FIG. 13 is a representation of the effect of one embodiment of the present invention where components similar to those found in FIG. 7 retain their previous indicia. The ECU 599 is connected to and controls the filter 508. The ECU 599 may be connected to an antenna 581 (or other receptor of electromagnetic energy, such as infrared or optical) and/or one or more local sensors 582 so as to receive data that affects ECU 599 control of the filter 508. In this embodiment of the present invention, the ECU controls the filter 508 so that the filter has an intermittent low pass impedance characteristic 577 (alternating between an open circuit and a closed circuit so that the low pass filter is in and out of the circuit) so as to intermittently attenuate (at a controllable switching rate, or duty cycle) high frequency corrosive noise. When the filter is attenuating the high frequency component of the corrosion noise, the high frequency spectral content of the electrochemical noise across the coating and protected material 550 has been significantly reduced; therefore, the noise signal is effectively been filtered so that it is a slowly changing voltage (i.e., not "spiky"). When the filter is not excising the corrosion noise, the noise characteristic of the coating 550 is noisy (spiky), indicating the zinc in the semiconductor layer is dissipating into the environment. In this situation, the ECU 599 controls the coating to act in an anti-foulant mode of operation. In other embodiments, the ECU 599 may control the filter 508 such that the filter 508 has a filter characteristic where the amplitude and/or frequency of predetermined corrosion noise frequencies are reduced and/or the filter 508 is intermittently connected. The reason why the filter is operated in a "pulsed" manner is to balance Zn depletion for anti-fouling against Zn preservation for anti-corrosion. Depletion rate can be controlled by setting the pulsed on/off cycles ranging from just above 0% (on) to always on (i.e., 100%). For example, a 50% on/off pulsed mode of operation, would have, over a predetermined period of time, the filter operating for 50% of the time, although not always at equal time intervals (i.e., not always with a 50% duty cycle). Furthermore, the pulsed operation may occur with period or aperiodic control waveforms.

Figure 14:
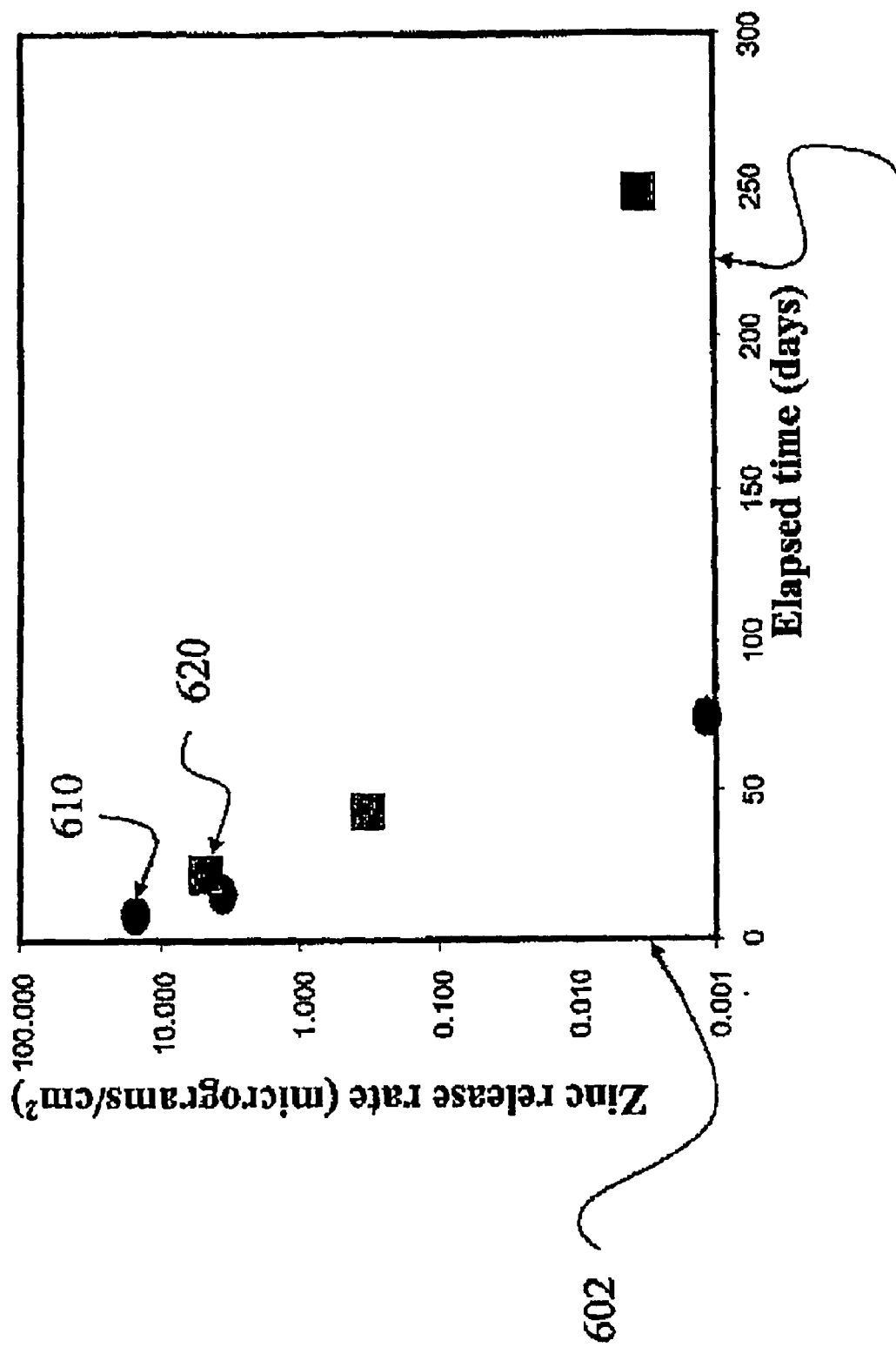
FIG. 14 is a graph comparing the zinc release rate (micrograms/cm$^2$) for a corrosion noise reducing system with and without an ECU.

FIG. 14 is a graph comparing the zinc release rate measured over time for a corrosion noise reducing system with and without an ECU. In this graph the zinc release rates of the two systems are displayed on a graph where the horizontal axis 601 measures elapsed time and days and the vertical axis 602 measures the zinc release rate in micrograms of zinc per $cm^2$. In the system where no ECU is used, the results are indicated by squares 620. In the other system, the zinc release rate was reduced by using a system with an ECU and the results are indicated by circles 610. The measurements were taken over a time period of approximately 300 days. A comparison of the two plots shows that the system without an ECU tended to release more zinc over the time period than did the system with an ECU and, then, had a shorter semiconductor coating lifespan.

Figure 15:
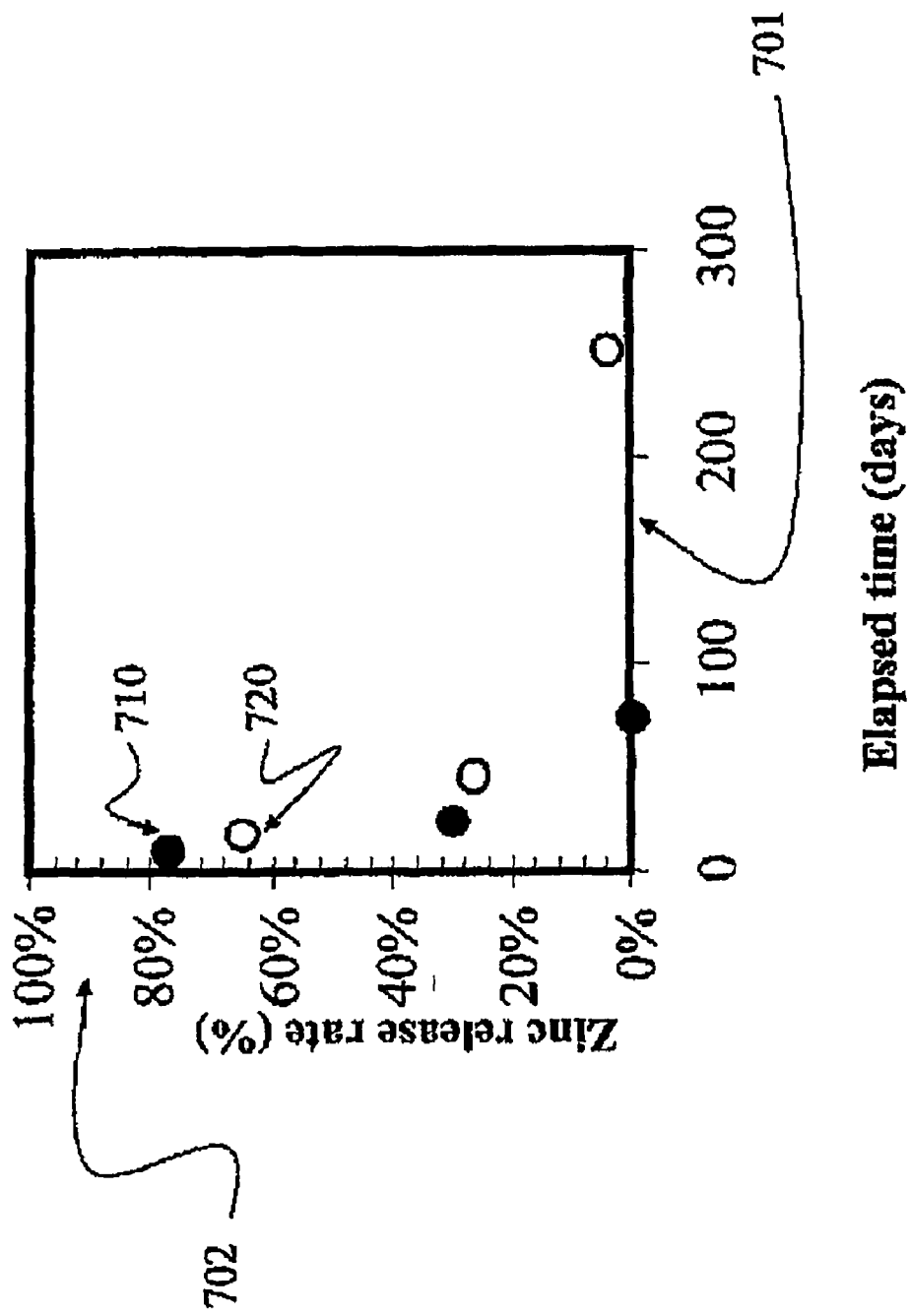
FIG. 15 is a graph comparing the zinc release rate (%) for a corrosion noise reducing system with and without an ECU.

FIG. 15 is a renormalization of the results found in FIG. 6, wherein the horizontal axis 701 represents time in days, and the vertical axis 702 represents the release of zinc as a percentage of total zinc released. In this graph, the results with an ECU indicated by circles 710 correspond to results 610 and results indicated by squares 720 correspond to results 620 in FIG. 14, respectively.

Figure 16:
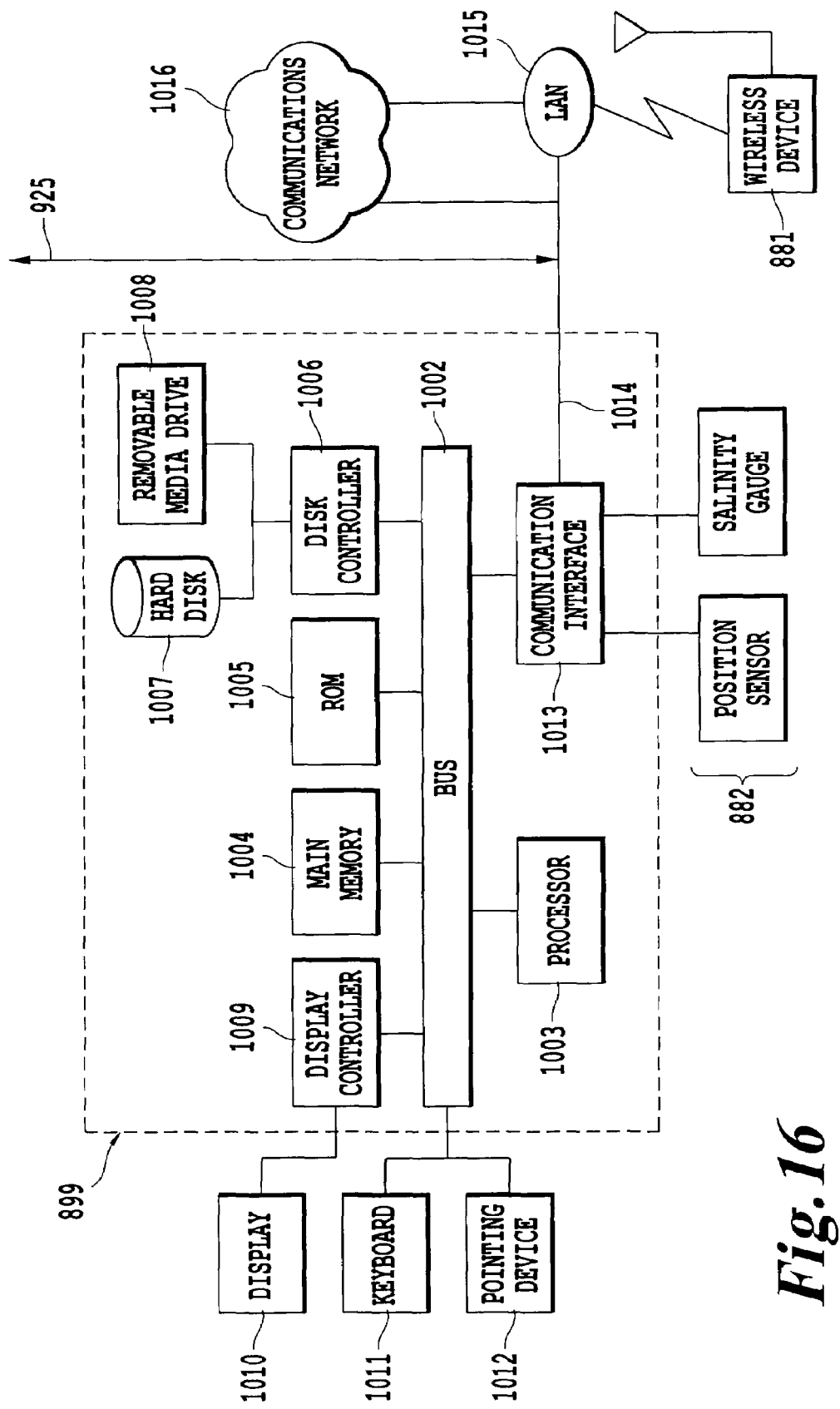
FIG. 16 is a block diagram of a computer system used in the present invention.

FIG. 16 shows a computer that can be used as an ECU control computer 899 in an embodiment of the present invention. The computer comprises a processor 1003, a main memory 1004, a ROM 1005, a system bus 1002, and is connected to various user interface devices 1010 through 1012 such as a monitor and, keyboard. In order to monitor physical conditions and other variables relevant to optimizing the operation of the anti-corrosive and anti-fouling measures of the present invention, the computer is connected to sensors 882 such as salinity and pressure gauges, geographic position sensors, etc.

A more detailed description of the ECU control computer 899 follows. The ECU control computer 899 includes a bus 1002 or other communication mechanism for communicating information (possibly in a wireless manner), and a processor 1003 coupled with the bus 1002 for processing the information. The ECU control computer 899 also includes a main memory 1004, such as a random access memory (RAM) or other dynamic storage device (e.g., dynamic RAM (DRAM), static RAM (SRAM), and synchronous DRAM (SDRAM)), coupled to the bus 1002 for storing information and instructions to be executed by processor 1003. In addition, the main memory 1004 may be used for storing temporary variables or other intermediate information during the execution of instructions by the processor 1003. The ECU control computer 899 further includes a read only memory (ROM) 1005 or other static storage device (e.g., programmable ROM (PROM), erasable PROM (EPROM), and electrically erasable PROM (EEPROM)) coupled to the bus 1002 for storing static information and instructions for the processor 1003.

The ECU control computer 899 also includes a disk controller 1006 coupled to the bus 1002 to control one or more storage devices for storing information and instructions, such as a magnetic hard disk 1007, and a removable media drive 1008 (e.g., floppy disk drive, read-only compact disc drive, read/write compact disc drive, compact disc jukebox, tape drive, and removable magneto-optical drive). The storage devices may be added to the computer system 950 using an appropriate device interface (e.g., small computer system interface (SCSI), integrated device electronics (IDE), enhanced-IDE (E-IDE), direct memory access (DMA), or ultra-DMA).

The ECU control computer 899 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The ECU control computer 899 may also include a display controller 1009 coupled to the bus 1002 to control a display 1010, such as a cathode ray tube (CRT), for displaying information to a computer user. The computer system includes input devices, such as a keyboard 1011 and a pointing device 1012, for interacting with a computer user and providing information to the processor 1003. The pointing device 1012, for example, may be a mouse, a trackball, or a pointing stick for communicating direction information and command selections to the processor 1003 and for controlling cursor movement on the display 1010. In addition, a printer may provide printed listings of data stored and/or generated by the ECU control computer 899.

The ECU control computer 899 performs a portion or all of the processing steps of the invention in response to the processor 1003 executing one or more sequences of one or more instructions contained in a memory, such as the main memory 1004. Such instructions may be read into the main memory 1004 from another computer readable medium, such as a hard disk 1007 or a removable media drive 1008. One or more processors in a multi-processing arrangement may also be employed to execute the sequences of instructions contained in main memory 1004. In alternative embodiments, hard-wired circuitry may be used in place of or in combination with software instructions. Thus, embodiments are not limited to any specific combination of hardware circuitry and software.

As stated above, the ECU control computer 899 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the ECU control computer 899, for driving a device or devices for implementing the invention, and for enabling the ECU control computer 899 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1003 for execution. A computer readable medium may take many forms, including but not limited to, non-volatile media, volatile media, and transmission media. Non-volatile media includes, for example, optical, magnetic disks, and magneto-optical disks, such as the hard disk 1007 or the removable media drive 1008. Volatile media includes dynamic memory, such as the main memory 1004. Transmission media includes coaxial cables, copper wire and fiber optics, including the wires that make up the bus 1002. Transmission media also may also take the form of acoustic or light waves, such as those generated during radio wave and infrared data communications.

Various forms of computer readable media may be involved in carrying out one or more sequences of one or more instructions to processor 1003 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the ECU control computer 899 may receive the data on the telephone line and use an infrared transmitter to convert the data to an infrared signal. An infrared detector coupled to the bus 1002 can receive the data carried in the infrared signal and place the data on the bus 1002. The bus 1002 carries the data to the main memory 1004, from which the processor 1003 retrieves and executes the instructions. The instructions received by the main memory 1004 may optionally be stored on storage device 1007 or 1008 either before or after execution by processor 1003.

The ECU control computer 899 also includes a communication interface 1013 coupled to the bus 1002. The communication interface 1013 provides a two-way data communication coupling to a network link 1014 that is connected to, for example, a local area network (LAN) 1015, or to another communications network 1016 such as the Internet. For example, the communication interface 1013 may be a network interface card to attach to any packet switched LAN. As another example, the communication interface 1013 maybe an asymmetrical digital subscriber line (ADSL) card, an integrated services digital network (ISDN) card or a modem to provide a data communication connection to a corresponding type of communications line. Wireless links may also be implemented. In any such implementation, the communication interface 1013 sends and receives electrical, electromagnetic or optical signals that carry digital data streams representing various types of information.

The network link 1014 typically provides data communication through one or more networks to other data devices. For example, the network link 1014 may provide a connection to another computer through a local network 1015 (e.g., a LAN) or through equipment operated by a service provider, which provides communication services through a communications network 1016. The local network 1014 and the communications network 1016 use, for example, electrical, electromagnetic, or optical signals that carry digital data streams, and the associated physical layer (e.g., CAT 5 cable, coaxial cable, optical fiber, etc). The signals through the various networks and the signals on the network link 1014 and through the communication interface 1013, which carry the digital data to and from the ECU control computer 899 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The ECU control computer 899 can transmit and receive data, including program code, through the network(s) 1015 and 1016, the network link 1014 and the communication interface 1013. Moreover, the network link 1014 may provide a connection through a LAN 1015 to a mobile device 881 such as a personal digital assistant (PDA) laptop computer, or cellular telephone.

The semiconductive coating of the present invention can be used in a variety of end uses. Chief among these end-uses is the prevention of corrosion of conductive structures.

The present system for preventing corrosion of conductive substrates comprises:
 (a) a semiconductor coating in conductive contact with at least part of the surface of the conductive structure;
 (b) a corrosive noise filter, comprising an electron sink, such as a battery or other power supply, along with a filter (or bank of filters), such as a capacitor, connected to the coated conductive substrate; and
 (c) a system for monitoring one or more parameters associated with the corrosion causing effects of geomagnetically induced currents or telluric currents in the coated conductive substrate and adjusting the corrosive noise filter to minimize the corrosion causing effects of the geomagnetically induced currents or telluric currents and minimize corrosion noise in the coated conductive substrate.

The present system also includes corrosion prevention method comprising:
 1) cleaning the external surface of a conductive structure;
 2) coating the external surface with the semiconductive coating of the present invention; and
 3) using an electronic filter to minimize corrosive noise in the system.

One key to the anti-corrosion method and system of the present invention is the measurement of corrosive noise generated by the entire system (including, but not limited to, the substrate, coating and filter components), and in particular the corrosive noise generated by GIC and/or telluric currents on a real time basis, and minimizing that noise by application of an electron Referring again to FIG. 6, the effect of the ECU upon semiconductive coating as well as overall performance was measured during the 249-day test period (FIG. 6). In this test, the zinc release rates decreased over time in both conditions as the coating "aged." However, the use of ECUs showed significantly greater reductions in zinc release rates, the extent of which are dependent on the duty cycle used to adjust or alternatively switch the filter in and out of the circuit. It is to be appreciated the duty cycle for controlling the level of zinc release (and therefore toxicity) depends on a number of parameters (such as measured corrosion noise, temperature, salinity, humidity, vessel speed, etc.) being dependent on the environmental conditions. The present invention addresses means of adjusting these rates through the ECU and associated control algorithms. The zinc release rates were lowered by a factor of 250, or as low as 0.001 micrograms/$cm^2$ per day, far below the U.S. Navy's maximum allowable rate of 15 micrograms per $cm^2$ per day (Office of Naval Research, S. McElvany). These experiments indicate the life of the semiconductive coating, with respect to zinc loss (quantity of Zn/$cm^2$ divided by the dissolution rate), can be significantly extended when used with the ECU. The results of the monitoring of potential, as shown in FIG. 6, demonstrate that the test panels without the ECU have a significantly lower potential, approximately 150 to 250 mV, based on the ECU value used. With the zinc oxidation rate depending exponentially on the magnitude of the potential, the zinc oxide potential will increase and the zinc potential will decrease with the electrical resistance of the zinc/zinc oxide boundary. The exponential sensitivity is indicated by the Tafel constant, specified for zinc as approximately 30 mV. This Tafel constant and the magnitude of the measured voltage differences predict that the relative passivation due to the ECU is between a factor of 150 and 4,000. In summary, both the zinc dissolution rate and potential data are consistent with the theory of operation of semiconductive—use of the ECU leads to a reduction in oxidation rate of the zinc, and significantly extends the life of the semiconductive coating. These benefits will be further enhanced by the present invention's use of measured and/or predetermined parameters relating to the effects of GIC or Telluric currents, and other parameters to include at least one of: temperature, salinity/water purity, humidity, age, short term duty cycle, long term duty cycle, immediate speed of vessel, vessel speed history, immediate geographic location, geographic location history, age of coating, thickness of coating, surface area coated, and shape of coated area.

The present invention can be tailored for the prevention of corrosion of conductive materials to include, but are not limited to: pipelines, petroleum storage tanks; government, including roads and bridges, and Navy, Coast Guard and Army Corps of Engineers projects; chemical industry; pulp and paper industries; power plants; railroad bridges and tracks and rail cars; manufactured steel buildings, such as farm silos and warehouses; water towers; offshore platforms; and other structures susceptible to the corrosive effects of GIC or telluric currents. The coating and ECU can also be adapted for devices and/or vehicles associated with space exploration, deep space missions, and satellite technology that are particularly susceptible to space weather effects.

The present invention can be operated to greatly reduce costly degradation of structures and to be a cost effective, durable, and environmentally friendly alternative to existing anti-fouling and anti-corrosion systems. The semiconductive coating can be applied on new structures during construction and on existing structures with relative ease. Further, due to the longevity of the semiconductive coating when used with the present system, the frequency of reapplication can be greatly reduced. With an ECU, owners of structures on which the semiconductive coating has been applied can receive the benefits of reduced maintenance costs, and extended structure life.

Regarding water tanks and towers, the ECU controlled corrosive noise reducing system of the present invention is EPA approved for use inside potable water containers. With proper application and with use of the ECU, the coating is expected to last for the design life of the tank. As a result of this longevity, water tank owners will not incur the recoating expenses that can be expected with protective coatings.

Obviously, numerous modifications and variations of the present invention are possible in light of the above teachings. It is therefore to be understood that within the scope of the appended claims, the invention maybe practiced otherwise than as specifically described herein.

What is claimed is:
1. A system for controlling space weather induced corrosion of a conductive structure susceptible thereto, comprising:
 a semiconductive coating disposed on said conductive structure;
 a filter connected to said coating and having a controllable filter characteristic; and
 a electronic control apparatus connected to said filter, comprising a connection to at least one of a local sensor, a data base, and remote control device, and configured to control said controllable filter characteristic in correspondence with at least one locally sensed parameter affected by space weather effects, and, optionally, one or more of an additional locally sensed parameter, a stored parameter and a remotely provided signal.

2. The system of claim 1, wherein said controllable filter characteristic is an impedance having the form of a low pass or notch filter.

3. The system of claim 1, wherein said filter comprises at least one:
of an active filter;
an adjustable passive filter; and
a fixed passive filter.

4. The system of claim 3, wherein said filter is a plurality of passive filters and said controllable filter characteristic is controlled by switching from one of said plurality of passive filters to another of said plurality of passive filters.

5. The system of claim 3, wherein said filter is a single adjustable passive filter.

6. The system of claim 1, wherein said locally sensed parameter affected by space weather effects is at least one member selected from the group consisting of searly warning data from observational satellites, spikes in electromagnetic activity, auroral zone electric currents, changes in the conductive structure's potential relative to ground, geomagnetic induced currents, telluric currents and combinations thereof, and, optionally, one or more of:
a corrosion noise parameter;
a salinity parameter;
a temperature parameter;
a geographic position parameter;
a time parameter;
a solution purity parameter;
a speed parameter;
a depth parameter; and
a pressure parameter.

7. The system of claim 1, wherein said stored parameter comprises at least one of:
a date of coating said object;
an object location history parameter;
a semiconductive coating duty cycle history parameter;
an object location history parameter;
a shape of coated area parameter; and
an object speed history parameter.

8. The system of claim 1, wherein said conductive structure comprises a metal selected from the group consisting of ferrous metals and conductive non-ferrous metals.

9. The system of claim 8, wherein said metal is steel.

10. The system of claim 8, wherein said metal is aluminum.

11. The system of claim 1, wherein said conductive structure is selected from the group consisting of pipelines, oil rigs, power plants, rail lines, and underwater structures.

12. The system of claim 1, wherein said semiconductive coating comprises a conductive organic polymer; and one or more metals, metal alloys, and non-metal semiconductive materials.

13. The system of claim 12, wherein said conductive organic polymer is a member selected from the group consisting of polyacetylenes, polyphenylenes, polyfurans, polythiophenes, polypyrroles, poly(arylene vinylenes), polyanilines, and doped compositions thereof.

14. The system of claim 12, wherein said one or more metals or metal alloys comprises a metal selected from the group consisting of Zn, Ti, Al, Ga, Ce, Mg, Ba, Cs, the corresponding metal oxides and alloys thereof.

15. The system of claim 12, wherein said one or more metals or metal alloys comprises a mixture of one or more metals selected from the group consisting of Zn, Ti, Al, Ga, Ce, Mg, Ba and Cs and one or more metal oxides obtained therefrom.

16. The system of claim 12, wherein said one or more metals or metal alloys is a combination of zinc/zinc oxide.

17. The system of claim 11, wherein said semiconductor coating further comprises one or more dyes or pigments.

18. An electronic control apparatus configured to control a corrosion noise reducing system including a controllable filter and a semiconductor coating applied to a conductive structure, comprising:
a first connection terminal configured to connect to said corrosion noise reducing system;
a second connection terminal configured to connect to at least one of a local sensor, a data base, and remote control device; and
a control mechanism configured to control said controllable filter via a control signal sent over said first connection terminal in correspondence with at least one locally sensed parameter affected by space weather effects, and, optionally, one or more of an additional locally sensed parameter, a stored parameter, and a remotely provided signal.

19. The apparatus of claim 18, wherein said controllable filter has a controllable filter characteristic which is an impedance having the form of a low pass or notch filter.

20. The apparatus of claim 19, wherein said controllable filter is a plurality of passive filters having impedances that differ one from the other and said controllable filter characteristic is controlled by switching from one of said plurality of passive filters to another of said plurality of passive filters.

21. The apparatus of claim 19, wherein said controllable filter is a single adjustable passive filter.

22. The apparatus of claim 19, wherein said locally sensed parameter affected by space weather effects is at least one member selected from the group consisting of early warning data from observational satellites, spikes in electromagnetic activity, auroral zone electric currents, changes in the conductive structure's potential relative to ground, geomagnetic induced currents, telluric currents and combinations thereof, and optionally, one or more of:
a corrosion noise parameter;
a salinity parameter;
a temperature parameter;
a geographic position parameter;
a time parameter;
a solution purity parameter;
a speed parameter;
a depth parameter; and
a pressure parameter.

23. The apparatus of claim 19, wherein said stored parameter comprises at least one of:
a date of coating said object,
an object location history parameter,
a semiconductive coating duty cycle history parameter,
an object location history parameter,
a shape of coated area parameter, and
an object speed history parameter.

24. The apparatus of claim 19, wherein said conductive structure comprises a metal selected from the group consisting of ferrous metals and conductive non-ferrous metals.

25. The apparatus of claim 24, wherein said metal is steel.

26. The apparatus of claim 24, wherein said metal is aluminum.

27. The apparatus of claim 19, wherein said conductive structure is selected from the group consisting of pipelines, oil rigs, power plants, rail lines, and underwater structures.

28. The apparatus of claim 19, wherein said semiconductive coating comprises a conductive organic polymer and one or more metals, metal alloys or non-metal semiconductive materials.

29. The apparatus of claim 28, wherein said conductive organic polymer is a member selected from the group consisting of polyacetylenes, polyphenylenes, polyfurans, polythiophenes, polypyrroles, poly(arylene vinylenes), polyanilines, and doped compositions thereof.

30. The apparatus of claim 29, wherein said one or more metals or metal alloys comprises a metal selected from the group consisting of Zn, Ti, Al, Ga, Ce, Mg, Ba, Cs, the corresponding metal oxides and alloys thereof.

31. The apparatus of claim 28, wherein said one or more metals or metal alloys comprises a mixture of one or more metals selected from the group consisting of Zn, Ti, Al, Ga, Ce, Mg, Ba and Cs and one or more metal oxides obtained therefrom.

32. The apparatus of claim 28, wherein said one or more metals or metal alloys is a combination of zinc/zinc oxide.

33. The apparatus of claim 28, wherein said semiconductive organic polymer coating further comprises one or more dyes or pigments.

34. A method for preventing corrosion of a conductive structure in contact with a corrosive environment, said method comprising:
connecting an electronic control unit to a controllable filter that is connected to a semiconductor coating disposed on said conductive structure;
filtering corrosive noise in said semiconductive coating with said controllable filter;
monitoring at least one parameter associated with space weather induced corrosion of said semiconductor coating; and
adjusting a filter characteristic of said controllable filter in correspondence with said at least one parameter.

35. The method of claim 34, wherein said filter characteristic is an impedance having the form of a low pass or notch filter.

36. The method of claim 34, wherein said controllable filter is a plurality of passive filters differing one from the other in at least said filter characteristic and said filter characteristic is controlled by switching from one of said plurality of passive filters to another of said plurality of passive filters.

37. The method of claim 34, wherein said controllable filter is a single adjustable passive filter.

38. The method of claim 34, wherein said at least one parameter associated with space weather induced corrosion is at least one member selected from the group consisting of searly warning data from observational satellites, spikes in electromagnetic activity, auroral zone electric currents, changes in the conductive structure's potential relative to ground, geomagnetic induced currents, telluric currents and combinations thereof, and, optionally, further comprises one or more of:
a corrosion noise parameter;
a salinity parameter;
a temperature parameter;
a geographic position parameter;
a time parameter;
a solution purity parameter;
a speed parameter;
a depth parameter;
a pressure parameter;
a date of coating said object;
an object location history parameter;
a semiconductive coating duty cycle history parameter;
an object location history parameter;
a shape of coated area parameter; and
an object speed history parameter.

39. The method of claim 34, wherein said conductive structure comprises a metal selected from the group consisting of ferrous metals and conductive non-ferrous metals.

40. The method of claim 39, wherein said metal is steel.

41. The method of claim 39, wherein said metal is aluminum.

42. The method of claim 34, wherein said conductive structure is selected from the group consisting of pipelines, oil rigs, power plants, rail lines and underwater structures.

43. The method of claim 34, wherein said semiconductor organic polymer coating comprises a conductive organic polymer and one or more metals, metal alloys or non-metal semiconductor materials.

44. The method of claim 43, wherein said conductive organic polymer is a member selected from the group consisting of polyacetylenes, polyphenylenes, polyfurans, polythiophenes, polypyrroles, poly(arylene vinylenes), polyanilines, and doped compositions thereof.

45. The method of claim 43, wherein said one or more metals or metal alloys comprises a metal selected from the group consisting of Zn, Ti, Al, Ga, Ce, Mg, Ba, Cs, the corresponding metal oxides and alloys thereof.

46. The method of claim 43, wherein said one or more metals or metal alloys comprises a mixture of one or more metals selected from the group consisting of Zn, Ti, Al, Ga, Ce, Mg, Ba and Cs and one or more metal oxides obtained therefrom.

47. The method of claim 43, wherein said one or more metals or metal alloys is a combination of zinc/zinc oxide.

48. The method of claim 43, wherein said semiconductor organic polymer coating further comprises one or more dyes or pigments.

49. A system for preventing corrosion of a conductive structure in contact with a corrosive environment, said conductive structure coated with a semiconductor coating, said method comprising:
means for filtering corrosive noise in said semiconductor coating;
means for monitoring at least one parameter associated with space weather induced corrosion of said semiconductor coating; and
means for adjusting said electronic filter in correspondence with said at least one parameter.

50. The system of claim 49, wherein said means for monitoring includes a computer program product.

* * * * *